United States Patent [19]
Cho et al.

[11] Patent Number: 5,780,472
[45] Date of Patent: Jul. 14, 1998

[54] PIPERAZINE DERIVATIVES AND METHODS FOR THE PREPARATION THEREOF AND COMPOSITIONS CONTAINING THE SAME

[75] Inventors: Eui-Hwan Cho; Sun-Gan Chung, both of Seoul; Joong-Ypoung Kim, Suweon; Sun-Hwan Lee, Songtan; Ho-Seok Kwon, Suweon; Byung-Chul Kim, Songtan; Jae-Myeong Kong, Suweon; Jea-Eung Lee, Hanam; Dong-Wook Kang, JinJu, all of Rep. of Korea

[73] Assignee: Samjin Pharmaceuticazl Co., Ltd., Seoul, Rep. of Korea

[21] Appl. No.: 676,174

[22] PCT Filed: Jan. 10, 1996

[86] PCT No.: PCT/KR96/00005

§ 371 Date: Jul. 15, 1996

§ 102(e) Date: Jul. 15, 1996

[87] PCT Pub. No.: WO96/21648

PCT Pub. Date: Jul. 18, 1996

[30] Foreign Application Priority Data

Jan. 11, 1995 [KR] Rep. of Korea ............ 1995-399
Nov. 24, 1995 [KR] Rep. of Korea ............ 1995-43607

[51] Int. Cl.[6] .............. A61K 31/495; C07D 401/12; C07D 401/14
[52] U.S. Cl. .............. 514/252; 544/360; 544/364; 544/357
[58] Field of Search .............. 544/360, 364; 514/252

[56] References Cited

FOREIGN PATENT DOCUMENTS 2-142770  5/1990  Japan .

OTHER PUBLICATIONS

Courant et al, *Eur. J. Med. Chem.* 28 pp. 821–824, 1993.

Kanoto, *Chemical Abstracts*, vol. 113, No. 172058 (1990) (Abstract of JP 02/42,770 May 31, 1990).

Ried et al, *Liebigs Ann. Chem.* pp. 693–698 (1980).

Primary Examiner—Emily Bernhardt
Attorney, Agent, or Firm—Birch, Stewart, Kolasch & Birch, LLP

[57] ABSTRACT

The present invention relates to novel compound of the general formula(I) and acid addition salt thereof.

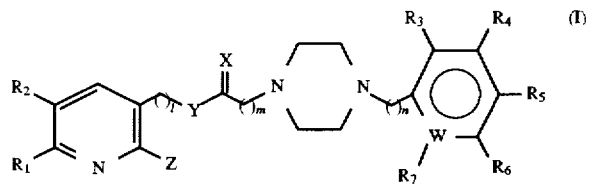

wherein $R_1$ and $R_2$ are independently hydrogen, $C_1$–$C_8$ alkyl or optionally substituted $C_3$–$C_6$ membered cycloalkyl containing $C_3$–$C_8$ ; $R_3$, $R_4$, $R_5$, $R_6$ and $R_7$ are independently hydrogen, halogen, hydroxy, nitro, $C_1$–$C_4$ lower ester, $C_1$–$C_4$ lower alkyl, $C_1$–$C_4$ lower alkoxy, aryl, arylalkoxy or unsaturated amine; l is an integer of 0–7; m and n are independently an integer of 0–1; W is carbon or nitrogen; X is oxygen, sulfur, optionally substituted imine; Y is nitrogen or oxygen; and Z is hydrogen, $C_1$–$C_8$ alkoxy, aryloxy, $C_1$–$C_4$ alkylamine, cycloamine containing $N_1$–$N_5$ or oxo group.

The present compounds of the above formula (I) has no only strong antimumor activities but lower toxicities, and accordingly are expected as novel antitumor agents.

6 Claims, No Drawings

PIPERAZINE DERIVATIVES AND METHODS FOR THE PREPARATION THEREOF AND COMPOSITIONS CONTAINING THE SAME

The present invention relates to new piperazine derivatives of the general formula(I)

wherein $R_1$ and $R_2$ are independently hydrogen, $C_1$–$C_8$ alkyl or optionally substituted $C_3$–$C_6$ membered cycloalkyl containing $C_3$–$C_8$; $R_3$, $R_4$, $R_5$, $R_6$ and $R_7$ are independently hydrogen, halogen, hydroxy, nitro, $C_1$–$C_4$ lower ester, $C_1$–$C_4$ lower alkyl, $C_1$–$C_4$ lower alkoxy, aryl, arylalkoxy or unsaturated amine; l is an integer of 0–7; m and n are independently an integer of 0–1; W is carbon or nitrogen; X is oxygen, sulfur, optionally substituted imine; Y is nitrogen or oxygen; and Z is hydrogen, $C_1$–$C_8$ alkoxy, aryloxy, $C_1$–$C_4$ alkylamine, cycloamine containing $N_1$–$N_5$ or oxo group.

$C_1$–$C_8$ alkyl means straight or branch alkyl group such as methyl, ethyl, propyl, butyl, isobutyl, tert-butyl, pentyl, iso-pentyl, hexyl, heptyl, octyl, 2-methyl-pentyl or the like.

$C_1$–$C_4$ lower alkyl means methyl, propyl, iso-propyl, n-butyl, iso-butyl, tert-butyl or the like.

Optionally substituted 3–6 membered cycloalkyl containing $C_3$–$C_8$ means substituted or unsubstituted cycloalkyl such as cyclopropyl, cyclobutyl, cyclopentyl, cyclohexyl, substituted cyclopropyl, substituted cyclopentyl, substituted cyclohexyl or the like.

$C_1$–$C_4$ lower ester means a carboxyl group esterified by lower alkyl group.

$C_1$–$C_4$ lower alkoxy means methoxy, ethoxy, propyloxy, isopropyloxy, butyloxy, isobutyloxy, tert-butyloxy group or the like.

Aryioxy means phenoxy, substituted phenoxy, naphthyloxy or substituted naphthyloxy or the like.

Cycloamine group containing $N_1$–$N_5$ means pyrrolidinyl, pyrrolinyl, imidazolyl, imidazolidinyl, pyrazolyl, pyrazolinyl, pyrazolidinyl, triazolyl, tetrazolyl, piperazinyl or the like.

The general formula(I) compound wherein Z is oxo has the structural formula(I') by tautomerism.

The present inventors had studied to find compounds having intensive antitumor activity for a long time. As the results, we finally found out the facts that the foresaid compounds of the general formula(I) and acid addition salts thereof have not only prominant antitumor activity but very low toxicity. Accordingly, the one object of the present invention is to provide the novel compounds of the general formula(I) and acid addition salts thereof having not only prominent antitumor activity but very low toxicity.

The other object of the present invention is to provide a process for the preparation of the compounds of general formula(I) and acid addition salts thereof.

The compounds of the present invention can be mixed with pharmaceutically acceptable vehicles by a known method to give pharmaceutical compositions and the pharmaceutical compositions can be used to prevent or treat various kinds of tumors of human beings or mammals.

Therefore, another object of the present invention is to provide pharmaceutical compositions containing the compounds of the general formula(I) and acid addition salts thereof as active ingredients.

Acids which can be reacted with the compounds of the general formula(I) to form acid addition salts are pharmaceutically acceptable inorganic or organic acids such as hydrochloric acid, bromic acid, sulfuric acid, phosphoric acid, nitric acid, formic acid, acetic acid, propionic acid, succinic acid, citric acid, maleic acid, malonic acid, glycolic acid, lactic acid, glycine, alanine, valine, luecine, isoleucine, serine, cysteine, cystine, asparaginic acid, glutamic acid, lysine, arginine, tyrosine, proline, methane sulfonic acid, ethane sulfonic acid, benzene sulfonic acid, toluene sulfonic acid or the like.

Vehicles which can be used in the preparation of pharmaceutical compositions containing the compounds of the general formula(I) as active ingredient are sweetening agent, binding agent, dissolving agent, aids for dissolution, wetting agent, emulsifying agent, isotonic agent, adsorbent, degrading agent, antioxident, antiseptics, lubricating agent, filler and perfume or the like such as lactose, dextrose, sucrose, mannitol, sorbitol, cellulose, glycine, sodium carboxy methyl cellulose, agar, talc, stearic acid, magnesium stearate, calcium stearate, magnesium aluminum silicate, starch, gelatine, tragacanth gum, methyl cellulose, glycine, silica, alginic acid, sodium alginate, water, ethanol, polyethylenglycol, polyvinyl pyrrolidone, sodium chloride, potassium chloride, orange essence, vanila aroma or the like.

Daily dosage of the compound of the general formula(I) may be varied depending on age, sex of patient and the degree of desease. Daily dosage is 1.0 mg to 5,000 mg and may be administered one to several times.

The compounds of the general formula(I) may be prepared by the following scheme I.

Scheme I wherein $R_1$, $R_2$, $R_3$, $R_4$, $R_5$, $R_6$, $R_7$, W, X, Y, Z, l and n are the same above and $Lie_1$ is a leaving group like hydrogen.

The compounds of the general formula(I) may be prepared by reacting a compound of the general formula(a) in the presense of —CX— group-providing agent with a compound of the general formula(b). —CX—group-providing agent comprises 1,1-carbonyldiimidazole, 1,1-carbonylthiodiimidazole, phosgene, thiophosgene, carbonyldiphenoxide, chlorophenoxyformate or the like. The reaction may be carried out in conventional organic solvent such as tetrahydrofuran, dichloromethane, acetonitrile or the like. And also the reaction is preferably carried out in the presence of scavenger such as conventional inorganic or organic base.

The reaction may be carried out between 3° C. and boiling point of the solvent used, preferably at 50° C.–100° C. for 5–48 hours, preferably for 10–24 hours. Quantity of —CX—group-providing agent may be 1–1.5 equivalent, preferably 1–1.1 equivalent to the starting compound.

The compounds of the general formula(I) may be prepared by Scheme II.

The compound of the general formula(c) may be prepared by reacting a compound of the general formula(a) in the presence of —CX—providing agent with piperazine in a solvent such as tetrahydrofuran, acetonitrile or the like under the same reaction condition of Scheme I. And then the compound of the general formula(I) may be prepared by reacting the compound of the general formula(c) in a solvent such as tetrahydrofuran or the like with a compound of the general formula (d) at 25°80° C. for 30 min–20 hours.

Scheme II

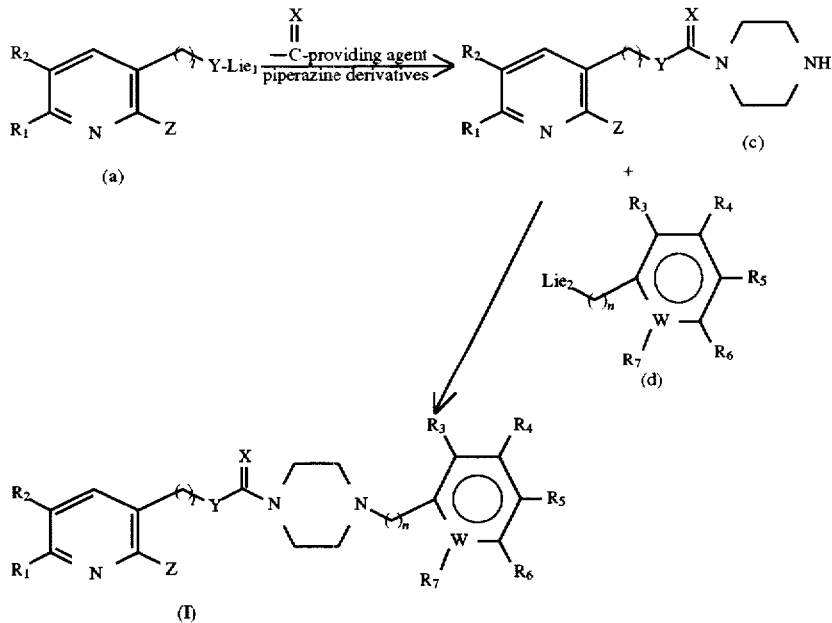

wherein $R_1$, $R_2$, $R_3$, $R_4$, $R_5$, $R_6$, $R_7$, W, X, Y, Z, l, n, and $Lie_1$ are the same above and $Lie_2$ is halogen.

The compounds of the general formula(I) may be prepared by Scheme III.

Scheme III

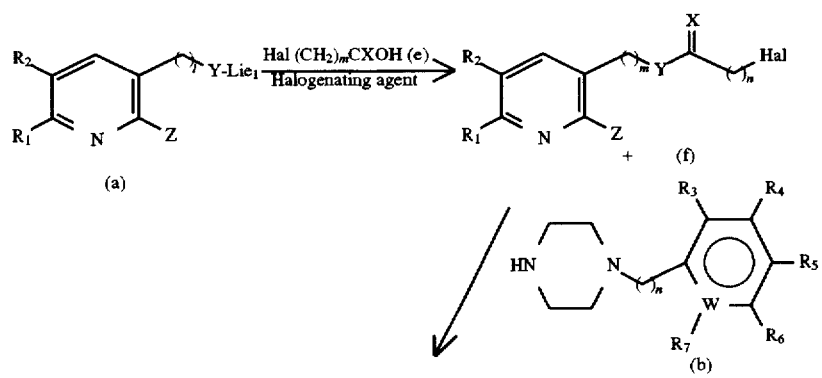

-continued
Scheme III

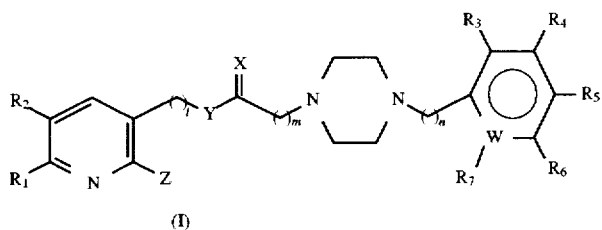

(I)

wherein, $R_1$, $R_2$, $R_3$, $R_4$, $R_5$, $R_6$, $R_7$, l, m, n, W, X, Y, Z and $Lie_1$ are the same above and Hal is halogen.

The compound of the general formula(f) may be prepared by reacting a compound of the general formula(a) with a compound of the general formula(e) and halogenating agent. And then the compound of the general formula(I) may be prepared by reacting the compound of the general fomula(f) with a compound of the general formula(b).

The compound of the general formula(I') may be prepared by Scheme IV.

Scheme IV

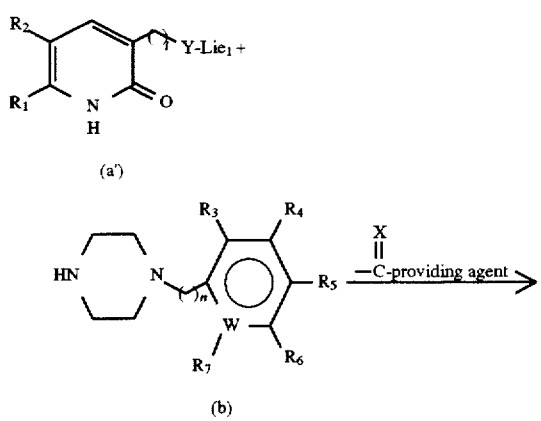

(b)

-continued
Scheme IV

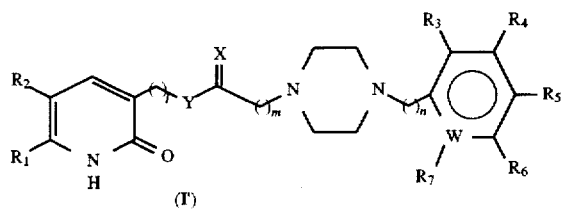

(I')

wherein $R_1$, $R_2$, $R_3$, $R_4$, $R_5$, $R_6$, $R_7$, l, m, n, W, X, Y, Z, and $Lie_1$ are the same above.

The compound of the general formula(I') may be prepared by reacting a compound of the general formula(a') in the presence of —CX—providing agent in a solvent like tetrahydrofuran or the like with a compound of the general formula (b) at ambient temperature for 30 min–5 hours.

The compounds of the general formula(I) may be prepared by Scheme V.

Scheme V

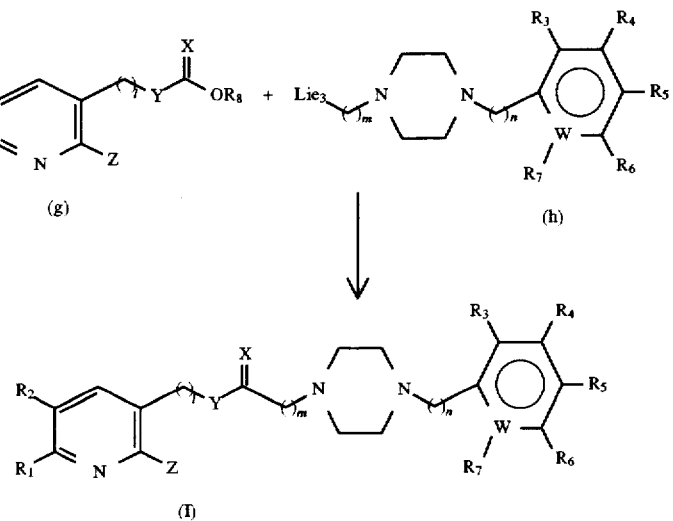

(I)

wherein, $R_1$, $R_2$, $R_3$, $R_4$, $R_5$, $R_6$, $R_7$, l, m, n, W, X, Y, Z are the same above and $R_8$ is $C_1$-$C_5$ alkyl or aryl group, $Lie_3$ is a leaving group like hydrogen. The compound of general formula(g) and the compound of general formula(h) may be prepared by condensing agent.

In the above reactions, if any acid material is formed, any basic material is preferably added as scavenger in order to eleminating the acid material from the reaction phase. Such basic material may be alkali metal hydroxide, alkali earth metal hydroxide, alkali metal oxide, alkali earth metal oxide, alkali metal carbonate, alkali earth metal carbonate, alkali metal hydrogen carbonate, alkali earth metal hydrogen carbonate such as sodium hydroxide, potassium hydroxide, calcium hydroxide, magnesium hydroxide, calcium oxide, magnesium oxide, potassium carbonate, sodium carbonate, calcium carbonate, magnesium carbonate, magnesium bicarbonate, sodium bicarbonate, calcium bicarbonate or the like and organic amines.

The compound of the general formula(a) is described in prior art (J. Med. Chem., 1992, 35, 3784, 3792) or may be prepared in a similar method to the art.

EXAMPLES:

The compounds of the general formula(I) and (I') are prepared by the following examples.

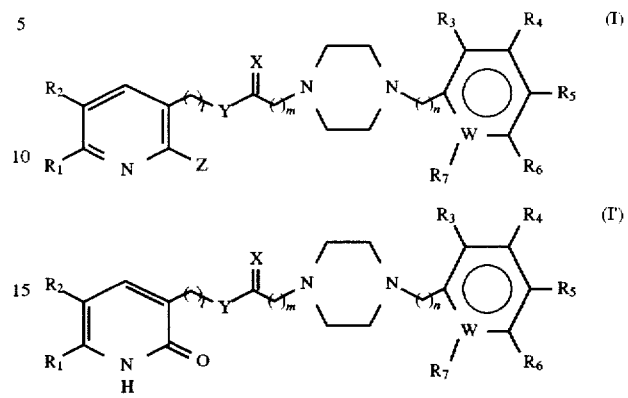

wherein $R_1$, $R_2$, $R_3$, $R_4$, $R_5$, $R_6$, $R_7$, l, m, n, W, X, Y, Z are the same above.

| ex. no | $R^1$ | $R^2$ | $R^3$ | $R^4$ | $R^5$ | $R^6$ | $R^7$ | X | Y | Z | W | l | m | n |
|---|---|---|---|---|---|---|---|---|---|---|---|---|---|---|
| 1 | Me | Et | OMe | H | H | H | H | O | NH | OMe | C | 0 | 0 | 0 |
| 2 | Me | Et | H | H | H | H | H | O | NH | OMe | C | 0 | 0 | 0 |
| 3 | Me | Et | H | H | OMe | H | H | O | NH | OMe | C | 0 | 0 | 0 |
| 4 | Me | Et | H | OMe | OMe | H | H | O | NH | OMe | C | 0 | 0 | 0 |
| 5 | Me | Et | OMe | H | OMe | H | H | O | NH | OMe | C | 0 | 0 | 0 |
| 6 | Me | Et | H | OMe | H | OMe | H | O | NH | OMe | C | 0 | 0 | 0 |
| 7 | Me | Et | H | OMe | OMe | OMe | H | O | NH | OMe | C | 0 | 0 | 0 |
| 8 | Me | Et | OEt | H | H | H | H | O | NH | OMe | C | 0 | 0 | 0 |
| 9 | Me | Et | OPh | H | H | H | H | O | NH | OMe | C | 0 | 0 | 0 |
| 10 | Me | Et | H | OPh | H | H | H | O | NH | OMe | C | 0 | 0 | 0 |
| 11 | Me | Et | F | H | H | H | H | O | NH | OMe | C | 0 | 0 | 0 |
| 12 | Me | Et | H | H | F | H | H | O | NH | OMe | C | 0 | 0 | 0 |
| 13 | Me | Et | H | F | H | F | H | O | NH | OMe | C | 0 | 0 | 0 |
| 14 | Me | Et | H | $CF_3$ | H | H | H | O | NH | OMe | C | 0 | 0 | 0 |
| 15 | Me | Et | Cl | H | H | H | H | O | NH | OMe | C | 0 | 0 | 0 |
| 16 | Me | Et | H | Cl | H | H | H | O | NH | OMe | C | 0 | 0 | 0 |
| 17 | Me | Et | Cl | H | H | H | Cl | O | NH | OMe | C | 0 | 0 | 0 |
| 18 | Me | Et | H | Cl | H | Cl | H | O | NH | OMe | C | 0 | 0 | 0 |
| 19 | Me | Et | Cl | H | Cl | H | H | O | NH | OMe | C | 0 | 0 | 0 |
| 20 | Me | Et | Cl | H | Cl | H | Cl | O | NH | OMe | C | 0 | 0 | 0 |
| 21 | Me | Et | Br | H | H | H | H | O | NH | OMe | C | 0 | 0 | 0 |
| 22 | Me | Et | H | Br | H | H | H | O | NH | OMe | C | 0 | 0 | 0 |
| 23 | Me | Et | H | H | Br | H | H | O | NH | OMe | C | 0 | 0 | 0 |
| 24 | Me | Et | Br | H | Br | H | H | O | NH | OMe | C | 0 | 0 | 0 |
| 25 | Me | Et | Br | H | H | Br | H | O | NH | OMe | C | 0 | 0 | 0 |
| 26 | Me | Et | Me | H | H | H | H | O | NH' | OMe | C | 0 | 0 | 0 |
| 27 | Me | Et | H | H | Me | H | H | O | NH | OMe | C | 0 | 0 | 0 |
| 28 | Me | Et | Me | Me | H | H | H | O | NH | OMe | C | 0 | 0 | 0 |
| 29 | Me | Et | H | Me | H | Me | H | O | NH | OMe | C | 0 | 0 | 0 |
| 30 | Me | Et | Me | H | H | H | Me | O | NH | OMe | C | 0 | 0 | 0 |
| 31 | Me | Et | H | H | i-Pr | H | H | O | NH | OMe | C | 0 | 0 | 0 |
| 32 | Me | Et | i-Pr | H | H | H | H | O | NH | OMe | C | 0 | 0 | 0 |
| 33 | Me | Et | H | H | n-Bu | H | H | O | NH | OMe | C | 0 | 0 | 0 |
| 34 | Me | Et | H | H | Ac | H | H | O | NH | OMe | C | 0 | 0 | 0 |
| 35 | Me | Et | Ph | H | H | H | H | O | NH | OMe | C | 0 | 0 | 0 |
| 36 | Me | Et | H | H | Ph | H | H | O | NH | OMe | C | 0 | 0 | 0 |
| 37 | Me | Et | OH | H | H | H | H | O | NH | OMe | C | 0 | 0 | 0 |
| 38 | Me | Et | H | OH | H | H | H | O | NH | OMe | C | 0 | 0 | 0 |
| 39 | Me | Et | H | H | OH | H | H | O | NH | OMe | C | 0 | 0 | 0 |
| 40 | Me | Et | H | H | OAc | H | H | O | NH | OMe | C | 0 | 0 | 0 |
| 41 | Me | Et | H | OAc | H | H | H | O | NH | OMe | C | 0 | 0 | 0 |
| 42 | Me | Et | H | H | $NO_2$ | H | H | O | NH | OMe | C | 0 | 0 | 0 |
| 43 | Me | Et | $NHCH_3$ | H | H | H | H | O | NH | OMe | C | 0 | 0 | 0 |
| 44 | Me | Et | H | H | H | -benzo- | | O | NH | OMe | C | 0 | 0 | 0 |
| 45 | Me | Et | H | H | H | -naphtho- | | O | NH | OMe | C | 0 | 0 | 0 |
| 46 | Me | Et | OMe | H | H | H | Me | O | NH | OMe | C | 0 | 0 | 0 |
| 47 | Me | Et | OMe | H | Me | H | H | O | NH | OMe | C | 0 | 0 | 0 |
| 48 | Me | Et | Me | H | H | OMe | H | O | NH | OMe | C | 0 | 0 | 0 |
| 49 | Me | Et | OMe | H | H | Cl | H | O | NH | OMe | C | 0 | 0 | 0 |
| 50 | Me | Et | Cl | H | H | OMe | H | O | NH | OMe | C | 0 | 0 | 0 |

-continued

| ex. no | R¹ | R² | R³ | R⁴ | R⁵ | R⁶ | R⁷ | X | Y | Z | W | l | m | n |
|---|---|---|---|---|---|---|---|---|---|---|---|---|---|---|
| | | | | | | | | | | | | (l, m, n = integer) | | |
| 51 | Me | Et | H | Cl | OMe | H | H | O | NH | OMe | C | 0 | 0 | 0 |
| 52 | Me | Et | H | OH | OMe | H | H | O | NH | OMe | C | 0 | 0 | 0 |
| 53 | Me | Et | H | OAc | OMe | H | H | O | NH | OMe | C | 0 | 0 | 0 |
| 54 | Me | Et | OMe | H | H | Ph | H | O | NH | OMe | C | 0 | 0 | 0 |
| 55 | Me | Et | Me | OH | H | H | H | O | NH | OMe | C | 0 | 0 | 0 |
| 56 | Me | Et | OH | H | H | H | Me | O | NH | OMe | C | 0 | 0 | 0 |
| 57 | Me | Et | OH | H | Me | H | H | O | NH | OMe | C | 0 | 0 | 0 |
| 58 | Me | Et | Me | H | H | Cl | H | O | NH | OMe | C | 0 | 0 | 0 |
| 59 | Me | Et | H | Cl | F | H | H | O | NH | OMe | C | 0 | 0 | 0 |
| 60 | Me | Et | OMe | H | H | H | H | O | NH | OMe | C | 1 | 0 | 0 |
| 61 | Me | Et | F | H | H | H | H | O | NH | OMe | C | 1 | 0 | 0 |
| 62 | Me | Et | H | H | F | H | H | O | NH | OMe | C | 1 | 0 | 0 |
| 63 | Me | Et | H | Cl | H | H | H | O | NH | OMe | C | 1 | 0 | 0 |
| 64 | Me | Et | H | H | F | H | H | O | NH | OMe | C | 2 | 0 | 0 |
| 65 | Me | Et | OMe | H | H | H | H | O | NH | OMe | C | 2 | 0 | 0 |
| 66 | Me | Et | OMe | H | H | H | H | O | NH | OMe | C | 3 | 0 | 0 |
| 67 | Me | Et | OMe | H | H | H | H | O | NH | OMe | C | 5 | 0 | 0 |
| 68 | Me | Et | OMe | H | H | H | H | O | NH | OMe | C | 7 | 0 | 0 |
| 69 | Me | Et | OMe | H | H | H | H | O | NH | OMe | C | 0 | 1 | 0 |
| 70 | Me | Et | H | Cl | H | H | H | O | NH | OMe | C | 0 | 1 | 0 |
| 71 | Me | Et | F | H | H | H | H | O | NH | OMe | C | 0 | 1 | 0 |
| 72 | Me | Et | H | H | H | H | H | O | NH | OMe | C | 0 | 0 | 1 |
| 73 | Me | Et | H | H | OMe | H | H | O | NH | OMe | C | 0 | 0 | 1 |
| 74 | Me | Et | OMe | H | H | H | H | O | NH | OMe | C | 0 | 0 | 1 |
| 75 | Me | Et | H | H | F | H | H | O | NH | OMe | C | 0 | 0 | 1 |
| 76 | Me | Et | OMe | H | H | H | H | O | NH | OEt | C | 0 | 0 | 0 |
| 77 | Me | Et | F | H | H | H | H | O | HH | OEt | C | 0 | 0 | 0 |
| 78 | Me | Et | H | Cl | H | H | H | O | NH | OEt | C | 0 | 0 | 0 |
| 79 | Me | Et | OEt | H | H | H | H | O | NH | OEt | C | 0 | 0 | 0 |
| 80 | Me | Et | OMe | H | H | H | H | O | NH | OPh | C | 0 | 0 | 0 |
| 81 | Me | Et | H | Cl | H | H | H | O | HH | OPh | C | 0 | 0 | 0 |
| 82 | Me | Et | H | OAc | H | H | H | O | NH | OPh | C | 0 | 0 | 0 |
| 83 | Me | Et | F | H | H | H | H | O | NH | OPh | C | 0 | 0 | 0 |
| 84 | Me | Et | H | Me | H | Me | H | O | NH | OPh | C | 0 | 0 | 0 |
| 85 | Me | Et | H | OMe | H | OMe | H | O | NH | OPh | C | 0 | 0 | 0 |
| 86 | Me | Et | H | Cl | H | Cl | H | O | NH | OPh | C | 0 | 0 | 0 |
| 87 | Me | Et | H | OH | OMe | H | H | O | NH | OPh | C | 0 | 0 | 0 |
| 88 | Me | Et | H | OH | H | H | H | O | NH | OPh | C | 0 | 0 | 0 |
| 89 | Me | Et | OMe | H | H | H | H | O | NH | NHCH₃ | C | 0 | 0 | 0 |
| 90 | Me | Et | H | OMe | H | OMe | H | O | NH | NHCH₃ | C | 0 | 0 | 0 |
| 91 | Me | Et | H | Cl | H | H | H | O | NH | NHCH₃ | C | 0 | 0 | 0 |
| 92 | Me | Et | OMe | H | H | H | H | O | NH | H | C | 0 | 0 | 0 |
| 93 | Me | Et | H | OMe | H | OMe | H | O | NH | H | C | 0 | 0 | 0 |
| 94 | Me | Et | H | Cl | H | H | H | O | NH | piperazine | C | 0 | 0 | 0 |
| 95 | Me | Et | H | Cl | H | H | H | O | NH | piperazine-Boc | C | 0 | 0 | 0 |
| 96 | Me | Et | OMe | H | H | H | H | O | NH | piperazine-Boc | C | 0 | 0 | 0 |
| 97 | Me | Et | OMe | H | H | H | H | S | NH | OMe | C | 0 | 0 | 0 |
| 98 | Me | Et | H | Cl | H | H | H | S | NH | OMe | C | 0 | 0 | 0 |
| 99 | Me | Et | F | H | H | H | H | S | NH | OMe | C | 0 | 0 | 0 |
| 100 | Me | Et | H | OMe | H | OMe | H | S | NH | OMe | C | 0 | 0 | 0 |
| 101 | Me | Et | H | Cl | H | Cl | H | S | NH | OMe | C | 0 | 0 | 0 |
| 102 | Me | Et | OMe | H | H | H | H | O | O | OMe | C | 0 | 0 | 0 |
| 103 | Me | Et | H | Cl | H | H | H | O | O | OMe | C | 0 | 0 | 0 |
| 104 | Me | Et | H | OMe | H | OMe | H | O | O | OMe | C | 0 | 0 | 0 |
| 105 | Me | Et | OMe | H | H | H | H | O | O | OMe | C | 1 | 0 | 0 |
| 106 | Me | Et | H | Cl | H | H | H | O | O | OMe | C | 1 | 0 | 0 |
| 107 | Me | Me | H | H | H | H | H | O | NH | OMe | C | 0 | 0 | 0 |
| 108 | Me | Me | OMe | H | H | H | H | O | NH | OMe | C | 0 | 0 | 0 |
| 109 | Me | Me | H | Cl | H | H | H | O | NH | OMe | C | 0 | 0 | 0 |
| 110 | Me | Me | F | H | H | H | H | O | NH | OMe | C | 0 | 0 | 0 |
| 111 | Me | Me | H | F | H | F | H | O | NH | OMe | C | 0 | 0 | 0 |
| 112 | Me | Me | OH | H | H | H | H | O | NH | OMe | C | 0 | 0 | 0 |
| 113 | Me | Me | H | OH | H | H | H | O | NH | OMe | C | 0 | 0 | 0 |
| 114 | Me | Me | H | H | OH | H | H | O | NH | OMe | C | 0 | 0 | 0 |
| 115 | Me | Me | H | OAc | H | H | H | O | NH | OMe | C | 0 | 0 | 0 |
| 116 | Me | Me | H | H | OAc | H | H | O | NH | OMe | C | 0 | 0 | 0 |
| 117 | Me | Me | H | OAc | OMe | H | H | O | NH | OMe | C | 0 | 0 | 0 |
| 118 | Me | Me | H | OMe | H | OMe | H | O | NH | OMe | C | 0 | 0 | 0 |
| 119 | Me | Me | Me | Me | H | H | H | O | NH | OMe | C | 0 | 0 | 0 |
| 120 | Me | Me | H | Me | H | Me | H | O | NH | OMe | C | 0 | 0 | 0 |
| 121 | Me | Me | Me | H | H | OMe | H | O | NH | OMe | C | 0 | 0 | 0 |
| 122 | Me | Me | OH | H | Me | H | H | O | NH | OMe | C | 0 | 0 | 0 |
| 123 | Me | Me | H | OH | OMe | H | H | O | NH | OMe | C | 0 | 0 | 0 |
| 124 | Me | Me | H | H | H | -benzo- | | O | NH | OMe | C | 0 | 0 | 0 |
| 125 | Me | Me | H | H | H | -naphtho- | | O | NH | OMe | C | 0 | 0 | 0 |

-continued

| ex. no | R¹ | R² | R³ | R⁴ | R⁵ | R⁶ | R⁷ | X | Y | Z | W | l | m | n |
|---|---|---|---|---|---|---|---|---|---|---|---|---|---|---|
| | | | | | | | | | | | | (l, m, n = integer) | | |
| 126 | Me | Me | H | Cl | H | H | H | S | NH | OMe | C | 0 | 0 | 0 |
| 127 | Me | Me | H | Cl | H | Cl | H | S | NH | OMe | C | 0 | 0 | 0 |
| 128 | Me | Me | OMe | H | H | H | H | S | NH | OMe | C | 0 | 0 | 0 |
| 129 | Me | Me | H | OMe | H | OMe | H | S | NH | OMe | C | 0 | 0 | 0 |
| 130 | —(CH₂)₃— | | OMe | H | H | H | H | O | NH | OMe | C | 0 | 0 | 0 |
| 131 | —(CH₂)₃— | | H | Cl | H | H | H | O | NH | OMe | C | 0 | 0 | 0 |
| 132 | —(CH₂)₃— | | F | H | H | H | H | O | NH | OMe | C | 0 | 0 | 0 |
| 133 | —(CH₂)₄— | | OMe | H | H | H | H | O | NH | OMe | C | 0 | 0 | 0 |
| 134 | —(CH₂)₄— | | H | Cl | H | H | H | O | NH | OMe | C | 0 | 0 | 0 |
| 135 | —(CH₂)₄— | | F | H | H | H | H | O | NH | OMe | C | 0 | 0 | 0 |
| 136 | Me | i-Pr | OMe | H | H | H | H | O | NH | OMe | C | 0 | 0 | 0 |
| 137 | Me | i-Pr | H | Cl | H | H | H | O | NH | OMe | C | 0 | 0 | 0 |
| 138 | Me | i-Pr | F | H | H | H | H | O | NH | OMe | C | 0 | 0 | 0 |
| 139 | H | H | H | H | H | H | H | O | NH | OMe | C | 0 | 0 | 0 |
| 140 | H | H | OMe | H | H | H | H | O | NH | OMe | C | 0 | 0 | 0 |
| 141 | H | H | H | H | OMe | H | H | O | NH | OMe | C | 0 | 0 | 0 |
| 142 | H | H | H | Cl | H | H | H | O | NH | OMe | C | 0 | 0 | 0 |
| 143 | Me | Et | NHCH₂CCH | H | H | H | H | O | NH | OMe | N | 0 | 0 | 0 |
| 144 | Me | Et | NHCH₂CCH | H | H | H | H | O | NH | OMe | N | 1 | 0 | 0 |
| 145 | Me | Et | NHCH₂CCH | H | H | H | H | O | NH | =O | N | 1 | 0 | 0 |
| 146 | Me | Et | N(CH₂Ph)₂ | H | H | H | H | O | NH | =O | N | 1 | 0 | 0 |
| 147 | Me | i-Pr | NHEt | H | H | H | H | O | NH | =O | N | 1 | 0 | 0 |
| 148 | Me | Et | OMe | H | H | H | H | O | NH | OMe | C | 0 | 0 | 0 |
| | | | | | | | | | | | | | HCl salt | |
| 149 | Me | Et | H | Cl | H | H | H | O | NH | OMe | C | 0 | 0 | 0 |
| | | | | | | | | | | | | | HCl salt | |

Example 1

1-[(5-ethyl-2-methoxy-6-methylpyridin-3-yl)aminocarbonyl]-4-(2-methoxyphenyl)piperazine Phenyl-N-(5-ethyl-2-methoxy-6-methylpyridin-3-yl)carbamate(0.29 g, 1.0 mmol) and 1-(2-methoxyphenyl)piperazine(0.19 g, 1.0 mmol) were dissolved in tetrahydrofuran(10 ml) and DBU(0.15 g, 1.0 mol) was added thereto and the mixture was stirred at room temperature for 2 hours. Then, the reaction mixture was concentrated and chromatographed to obtain 0.33 g of the titled compound.

yield: 89%; ¹H-NMR(500 MHZ, CDCl₃): δ 1.17(3H,t,J=7.5 Hz), 2.37(3H,s), 2.55(2H,q,J=7.5 Hz), 3.11(4H,t,J=4.6 Hz), 3.69(4H,t,J=5.0 Hz), 3.88(1H,s), 3.98(3H,s), 6.89(1H, s), 6.94(3H,m), 7.05(1H,m), 8.21(1H,s).

Elemental Analysis: $C_{21}H_{28}N_4O_3$: Calc., C.65.60, H.7.34, N.14.57. Found, C.66.10, H.7.25, N.14.57.

Example 2

1-[(5-ethyl-2-methoxy-6-methylpyridin-3-yl)aminocarbonyl]-4-phenylpiperazine

Phenyl-N-(5-ethyl-2-methoxy-6-methylpyridin-3-yl)carbamate and 1-phenylpiperazine were reacted by the same way with the example 1 to obtain the titled compound.

yield: 86%

Example 3

1-[(5-ethyl-2-methoxy-6-methylpyridin-3-yl)aminocarbonyl]-4-(4-methoxyphenyl)piperazine Phenyl-N-(5-ethyl-2-methoxy-6-methylpyridin-3-yl)carbamate and 1-(4-methoxyphenyl)piperazine were reacted by the same way with the example 1 to obtain the titled compound.

yield: 78%

Example 4

1-[(5-ethyl-2-methoxy-6-methylpyridin-3-yl)aminocarbonyl]-4-(3,4-dimethoxyphenyl)piperazine Phenyl-N-(5-ethyl-2-methoxy-6-methylpyridin-3-yl)carbamate and 1-(3,4-dimethoxyphenyl)piperazine were reacted by the same way with the example 1 to obtain the titled compound.

yield: 69%

Example 5

1-[(5-ethyl-2-methoxy-6-methylpyridin-3-yl)aminocarbonyl]-4-(2,4-dimethoxyphenyl)piperazine Phenyl-N-(5-ethyl-2-methoxy-6-methylpyridin-3-yl)carbamate and 1-(2,4-dimethoxyphenyl)piperazine were reacted by the same way with the example 1 to obtain the titled compound.

yield: 77%

Example 6

1-[(5-ethyl-2-methoxy-6-methylpyridin-3-yl)aminocarbonyl]-4-(3,5-dimethoxyphenyl)piperazine Phenyl-N-(5-ethyl-2-methoxy-6-methylpyridin-3-yl)carbamate and 1-(3,5-dimethoxyphenyl)piperazine were reacted by the same way with the example 1 to obtain the titled compound.

yield: 82%

Example 7

1-[(5-ethyl-2-methoxy-6-methylpyridin-3-yl)aminocarbonyl]-4-(3,4,5-trimethoxyphenyl)piperazine Phenyl-N-(5-ethyl-2-methoxy-6-methylpyridin-3-yl)carbamate and 1-(3,4,5-trimethoxyphenyl)piperazine were reacted by the same way with the example 1 to obtain the titled compound.

yield: 52%

Example 8

1-[(5-ethyl-2-methoxy-6-methylpyridin-3-yl)aminocarbonyl]-4-(2-ethoxyphenyl)piperazine Phenyl-N-(5-ethyl-2-methoxy-6-methylpyridin-3-yl)carbamate and 1-(2-ethoxyphenyl)piperazine were reacted by the same way with the example 1 to obtain the titled compound.

yield: 78%

Example 9
1-[(5-ethyl-2-methoxy-6-methylpyridin-3-yl) aminocarbonyl]-4-(2-phenoxyphenyl)piperazine Phenyl-N-(5-ethyl-2-methoxy-6-methylpyridin-3-yl) carbamate and 1-(2-phenoxyphenyl)piperazine were reacted by the same way with the example 1 to obtain the titled compound.

yield: 69%

Example 10
1-[(5-ethyl-2-methoxy-6-methylpyridin-3-yl) aminocarbonyl]-4-(3-phenoxyphenyl)piperazine Phenyl-N-(5-ethyl-2-methoxy-6-methylpyridin-3-yl) carbamate and 1-(3-phenoxyphenyl)piperazine were reacted by the same way with the example 1 to obtain the titled compound.

yield: 72%

Example 11
1-[(5-ethyl-2-methoxy-6-methylpyridin-3-yl)-aminocarbonyl]-4-(2-fluorophenyl)piperazine Phenyl-N-(5-ethyl-2-methoxy-6-methylpyridin-3-yl) carbamate and 1-(2-fluorophenyl)piperazine were reacted by the same way with the example 1 to obtain the titled compound.

yield: 67%

Example 12
1-[(5-ethyl-2-methoxy-6-methylpyridin-3-yl) aminocarbonyl]-4-(4-fluorophenyl)piperazine Phenyl-N-(5-ethyl-2-methoxy-6-methylpyridin 3-yl) carbamate and 1-(4-fluorophenyl)piperazine were reacted by the same way with the example 1 to obtain the titled compound.

yield: 81%

Example 13
1-[(5-ethyl-2-methoxy-6-methylpyridine-3-yl) aminocarbonyl]-4-(3,5-difluorophenyl)piperazine Phenyl-N-(5-ethyl-2-methoxy-6-methylpyridin-3-yl) carbamate and 1-(3,5-difluorophenyl)piperazine were reacted by the same way with the example 1 to obtain the titled compound.

yield: 69%

Example 14
1[(5-ethyl-2-methoxy-6-methylpyridin-3-yl) aminocarbonyl]-4-(α, α, α-trifluoro-m-tolyl)piperazine Phenyl-N-(5-ethyl-2-methoxy-6-methylpyridin-3-yl) carbamate and 1-(α, α, α-trifluoro-m-tolyl)piperazine were reacted by the same way with the example 1 to obtain the titled compound.

yield: 67%

Example 15
1-[(5-ethyl-2-methoxy-6-methylpyridin-3-yl) aminocarbonyl]-4-(2-chlorophenyl)piperazine Phenyl-N-(5-ethyl-2-methoxy-6-methylpyridin-3-yl) carbamate and 1-(2-chlorophenyl)piperazine were reacted by the same way with the example 1 to obtain the titled compound.

yield: 82%

Example 16
1-[(5-ethyl-2-methoxy-6-methylpyridin-3-yl) aminocarbonyl]-4-(3-chlorophenyl)piperazine Phenyl-N-(5-ethyl-2-methoxy-6-methylpyridin-3-yl) carbamate and 1-(3-chlorophenyl)piperazine were reacted by the same way with the example 1 to obtain the titled compound.

yield: 84%

Example 17
1-[(5-ethyl-2-methoxy-6-methylpyridin-3-yl) aminocarbonyl]-4-(2,6-dichlorophenyl)piperazine Phenyl-N-(5-ethyl-2-methoxy-6-methylpyridin-3-yl) carbamate and 1-(2,6-dichlorophenyl)piperazine were reacted by the same way with the example 1 to obtain the titled compound.

yield: 80%

Example 18
1-[(5-ethyl-2-methoxy-6-methylpyridin-3-yl) aminocarbonyl]-4-(3,5-dichlorophenyl)piperazine Phenyl-N-(5-ethyl-2-methoxy-6-methylpyridin-3-yl) carbamate and 1-(3,5-dichlorophenyl)piperazine were reacted by the same way with the example 1 to obtain the titled compound.

yield: 69%

Example 19
1-[(5-ethyl-2-methoxy-6-methylpyridin-3-yl) aminocarbonyl]-4-(2,4-dichlorophenyl)piperazine Phenyl-N-(5-ethyl-2-methoxy-6-methylpyridin-3-yl) carbamate and 1-(2,4-dichlorophenyl)piperazine were reacted by the same way with the example 1 to obtain the titled compound.

yield: 72%

Example 20
1-[(5-ethyl-2-methoxy-6-methylpyridin-3-yl) aminocarbonyl]-4-(2,4,6-trichlorophenyl)piperazine Phenyl-N-(5-ethyl-2-methoxy-6-methylpyridin-3-yl) carbamate and 1-(2,4,6-trichlorophenyl)piperazine were reacted by the same way with the example 1 to obtain the titled compound.

yield: 54%

Example 21
1-[(5-ethyl-2-methoxy-6-methylpyridin-3-yl) aminocarbonyl]-4-(2-bromophenyl)piperazine Phenyl-N-(5-ethyl-2-methoxy-6-methylpyridin-3-yl) carbamate and 1-(2-bromophenyl)piperazine were reacted by the same way with the example 1 to obtain the titled compound.

yield: 58%

Example 22
1-[(5-ethyl-2-methoxy-6-methylpyridin-3-yl) aminocarbonyl]-4-(3-bromophenyl)piperazine Phenyl-N-(5-ethyl-2-methoxy-6-methylpyridin-3-yl) carbamate and 1-(3-bromophenyl)piperazine were reacted by the same way with the example 1 to obtain the titled compound.

yield: 65%

Example 23
1-[(5-ethyl-2-methoxy-6-methylpyridin-3-yl) aminocarbonyl]-4-(4-bromophenyl)piperazine Phenyl-N-(5-ethyl-2-methoxy-6-methylpyridin-3-yl) carbamate and 1-(4-bromophenyl)piperazine were reacted by the same way with the example 1 to obtain the titled compound.

yield: 64%

Example 24
1-[(5-ethyl-2-methoxy-6-methylpyridin-3-yl) aminocarbonyl]-4-(2,4-dibromophenyl)piperazine Phenyl-N-(5-ethyl-2-methoxy-6-methylpyridin-3-yl) carbamate and 1-(2,4-dibromoplhenyl)piperazine were reacted by the same way with the example 1 to obtain the titled compound.
yield: 68%

Example 25
1-[(5-ethyl-2-methoxy-6-methylpyridin-3-yl) aminocarbonyl]-4-(2,5-dibromophenyl)piperazine Phenyl-N-(5-ethyl-2-methoxy-6-methylpyridin-3-yl) carbamate and 1-(2,5-dibromophenyl)piperazine were reacted by the same way with the example 1 to obtain the titled compound.
yield: 66%

Example 26
1-[(5-ethyl-2-methoxy-6-methylpyridin-3-yl) aminocarbonyl]-4-(2-tolyl)piperazine Phenyl-N-(5-ethyl-2-methoxy-6-methylpyridin-3-yl) carbamate and 1-(2-tolyl)piperazine were reacted by the same way with the example 1 to obtain the titled compound.
yield: 89%

Example 27
1-[(5-ethyl-2-methoxy-6-methylpyridin-3-yl) aminocarbonyl]-4-(4-methylphenyl)piperazine Phenyl-N-(5-ethyl-2-methoxy-6-methylpyridin-3-yl) carbamate and 1-(4-methylphenyl)piperazine were reacted by the same way with the example 1 to obtain the titled compound.
yield: 87%

Example 28
1-[(5-ethyl-2-methoxy-6-methylpyridin-3-yl) aminocarbonyl]-4-(2,3-dimethylphenyl)piperazine Phenyl-N-(5-ethyl-2-methoxy-6-methylpyridin-3-yl) carbamate and 1-(2,3-dimethylphenyl)piperazine were reacted by the same way with the example 1 to obtain the titled compound.
yield: 82%

Example 29
1-[(5-ethyl-2-methoxy-6-methylpyrdin-3-yl) aminocarbonyl]-4-(3,5-dimethylphenyl)piperazine Phenyl-N-(5-ethyl-2-methoxy-6-methylpyridin-3-yl) carbamate and 1-(3,5-dimethylphenyl)piperazine were reacted by the same way with the example 1 to obtain the titled compound.
yield: 68%

Example 30
1-[(5-ethyl-2-methoxy-6-methylpyridin-3-yl) aminocarbonyl]-4-(2,6-dimethylphenyl)piperazine Phenyl-N-(5-ethyl-2-methoxy-6-methylpyridin-3-yl) carbamate and 1-(2,6-dimethylphenyl)piperazine were reacted by the same way with the example 1 to obtain the titled compound
yield: 80%

Example 31
1-[(5-ethyl-2-methoxy-6-methylpyridin-3-yl) aminocarbonyl]-4-(4-isopropylphenyl)piperazine Phenyl-N-(5-ethyl-2-methoxy-6-methylpyridin-3-yl) carbamate and 1-(4-isopropylphenyl)piperazine were reacted by the same way with the example 1 to obtain the titled compound.
yield: 68%

Example 32
1-[(5-ethyl-2-methoxy-6-methylpyridin-3-yl) aminocarbonyl]-4-(2-isopropylphenyl)piperazine Phenyl-N-(5-ethyl-2-methoxy-6-methylpyridin-3-yl) carbamate and 1-(2-isopropylphenyl)piperazine were reacted by the same way with the example 1 to obtain the titled compound.
yield: 65%

Example 33
1-[(5-ethyl-2-methoxy-6-methylpyridin-3-yl) aminocarbonyl]-4-(4-normalbutylphenyl)piperazine Phenyl-N-(5-ethyl-2-methoxy-6-methylpyridin-3-yl) carbamate and 1-(4-normalbutylphenyl)piperazine were reacted by the same way with the example 1 to obtain the titled compound.
yield: 57%

Example 34
1-[(5-ethyl-2-methoxy-6-methylpyridin-3-yl) aminocarbonyl]-4-(4-acetylphenyl)piperazine Phenyl-N-(5-ethyl-2-methoxy-6-methylpyridin-3-yl) carbamate and 1-(4-acetylphenyl)piperazine were reacted by the same way with the example 1 to obtain the titled compound.
yield: 67%

Example 35
1-[(5-ethyl-2-methoxy-6-methylpyridin-3-yl) aminocarbonyl]-4-(2-biphenyl)piperazine Phenyl-N-(5-ethyl-2-methoxy-6-methylpyridin-3-yl) carbamate and 1-(2-biphenyl)piperazine were reacted by the same way with the example 1 to obtain the titled compound.
yield: 82%

Example 36
1-[(5-ethyl-2-methoxy-6-methylpyridin-3-yl) aminocarbonyl]-4-(4-biphenyl)piperazine Phenyl-N-(5-ethyl-2-methoxy-6-methylpyridin-3-yl) carbamate and 1-(4-biphenyl)piperazine were reacted by the same way with the example 1 to obtain the titled compound.
yield: 81%

Example 37
1-[(5-ethyl-2-methoxy-6-methylpyridin-3-yl) aminocarbonyl]-4-(2-hydroxyphenyl)piperazine Phenyl-N-(5-ethyl-2-methoxy-6-methylpyridin-3-yl) carbamate and 1-(2-hydroxyphenyl)piperazine were reacted by the same way with the example 1 to obtain the titled compound.
yield: 59%

Example 38
1-[(5-ethyl-2-methoxy-6-methylpyridin-3-yl) aminocarbonyl]-4-(3-hydroxyphenyl)piperazine Phenyl-N-(5-ethyl-2-methoxy-6-methylpyridin-3-yl) carbamate and 1-(3-hydroxyphenyl)piperazine were reacted by the same way with the example 1 to obtain the titled compound.
yield: 63%

Example 39
1-[(5-ethyl-2-methoxy-6-methylpyridin-3-yl) aminocarbonyl]-4-(4-hydroxyphenyl)piperazine Phenyl-N-(5-ethyl-2-methoxy-6-methylpyridin-3-yl) carbamate and 1-(4-hydroxyphenyl)piperazine were reacted by the same way with the example 1 to obtain the titled compound.
yield: 58%

Example 40
1-[(5-ethyl-2-methoxy-6-methylpyridin-3-yl) aminocarbonyl]-4-(4-acetoxyphenyl)piperazine

Example 41
1-[(5-ethyl-2-methoxy-6-methylpyridin-3-yl)aminocarbonyl]-4-(3-acetoxyphenyl)piperazine Phenyl-N-(5-ethyl-2-methoxy-6-methylpyridin-3-yl) carbamate and 1-(3-acetoxyphenyl)piperazine were reacted by the same way with the example 1 to obtain the titled compound.

yield: 87%

Example 42
1-[(5-ethyl-2-metoxy-6-methylpyridin-3-yl)aminocarbonyl]-4-(4-nitrophenyl) piperazine Phenyl-N-(5-ethyl-2-methoxy-6-methylpyridin-3-yl) carbamate and 1-(4-nitrophenyl)piperazine were reacted by the same way with the example 1 to obtain the titled compound.

yield: 70%

Example 43
1-[(5-ethyl-2-methoxy-6-methylpyridin-3-yl)aminocarbonyl]-4-[(2-methylamino)phenyl]piperazine Phenyl-N-(5-ethyl-2-methoxy-6-methylpyridin-3-yl) carbamate and 1-[2-(methylamino)phenyl]piperazine were reacted by the same way with the example 1 to obtain the titled compound.

yield: 59%

Example 44
1-[(5-ethyl-2-methoxy-6-methylpyridin-3-yl)aminocarbonyl]-4-(1-naphthyl)piperazine Phenyl-N-(5-ethyl-2-methoxy-6-methylpyridin-3-yl) carbamate and 1-(1-naphthyl)piperazine were reacted by the same way with the example 1 to obtain the titled compound.

yield: 63%

Example 45
1-[(5-ethyl-2-methoxy-6-methylpyridin-3-yl)aminocarbonyl]-4-(1-anthryl)piperazine Phenyl-N-(5-ethyl-2-methoxy-6-methylpyridin-3-yl) carbamate and 1-(1-anthryl)piperazine were reacted by the same way with the example 1 to obtain the titled compound.

yield: 57%

Example 46
1-[(5-ethyl-2-methoxy-6-methylpyridin-3-yl)aminocarbonyl]-4-(2-methoxy-6-methylphenyl)piperazine Phenyl-N-(5-ethyl-2-methoxy-6-methylpyridin-3-yl) carbamate and 1-(2-methoxy-6-methylphenyl)piperazine were reacted by the same way with the example 1 to obtain the titled compound.

yield: 67%

Example 47
1-[(5-ethyl-2-methoxy-6-methylpyridin-3-yl)aminocarbonyl]-4-(2-methoxy-5-methylphenyl)piperazine Phenyl-N-(5-ethyl-2-methoxy-6-methylpyridin-3-yl) carbamate and 1-(2-methoxy-5-phenyl)piperazine were reacted by the same way with the example 1 to obtain the titled compound.

yield: 62%

Example 48
1-[(5-ethyl-2-methoxy-6-methylpyridin-3-yl)aminocarbonyl]-4-(5-methoxy-2-methylphenyl)piperazine Phenyl-N-(5-ethyl-2-methoxy-6-methylpyridin-3-yl) carbamate and 1-(5-methoxy-2-methylphenyl)piperazine were reacted by the same way with the example 1 to obtain the titled compound.

yield: 66%

Example 49
1-[(5-ethyl-2-methoxy-6-methylpyridin-3-yl)aminocarbonyl]-4-(5-chloro-2-methioxyphenyl)piperazine Phenyl-N-(5-ethyl-2-methoxy-6-methylpyridin-3-yl) carbamate and 1-(5-chloro-2-methoxyphenyl)piperazine were reacted by the same way with the example 1 to obtain the titled compound.

yield: 69%

Example 50
1-[(5-ethyl-2-methoxy-6-methylpyridin-3-yl)aminocarbonyl]-4-(2-chloro-5-methoxyphenyl)piperazine Phenyl-N-(5-ethyl-2-methoxy-6-methylpyridin3-yl) carbamate and 1-(2-chloro-5-methoxyphenyl)piperazine were reacted by the same way with the example 1 to obtain the titled compound.

yield: 70%

Example 51
1-[(5-ethyl-2-methoxy-6-methylpyridin-3-yl)aminocarbonyl]-4-(3-chloro-4-methoxyphenyl)piperazine Phenyl-N-(5-ethyl-2-methoxy-6-methylpyridin-3-yl) carbamate and 1-(3-chloro-4-methoxyphenyl)piperazine were reacted by the same way with the example 1 to obtain the titled compound.

yield: 62%

Example 52
1-[(5-ethyl-2-methoxy-6-methylpyridin-3-yl)aminocarbonyl]-4-(3-hydroxy-4-methoxyphenyl)piperazine Phenyl-N-(5-ethyl-2-methoxy-6-methylpyridin-3-yl) carbamate and 1-(3-hydroxy-4-methoxyphenyl)piperazine were reacted by the same way with the example 1 to obtain the titled compound. yield: 59%

Example 53
1-[(5-ethyl-2-methoxy-6-methylpyridin-3-yl)aminocarbonyl]-4-(3-acetoxy-4-methoxyphenyl)piperazine Phenyl-N-(5-ethyl-2-methoxy-6-methylpyridin-3-yl) carbamate and 1-(3-acetoxy-4-methoxyphenyl)piperazine were reacted by the same way with the example 1 to obtain the titled compound. 25 yield: 62%

Example 54
1-[(5-ethyl-2-methoxy-6-methylpyridin-3-yl)aminocarbonyl]-4-[(2-methoxy-5-phenyl)phenyl]piperazine Phenyl-N-(5-ethyl-2-methoxy-6-methylpyridin-3-yl) carbamate and 1-[(2-methoxy-5-phenyl)phenyl]piperazine were reacted by the same way with the example 1 to obtain the titled compound. yield: 67%

Example 55
1-[(5-ethyl-2-methoxy-6-methylpyridin-3-yl)aminocarbonyl]-4-(3-hydroxy-2-methylphenyl)piperazine Phenyl-N-(5-ethyl-2-methoxy-6-methylpyridin-3-yl) carbamate and 1-(3-hydroxy-2-methylphenyl)piperazine were reacted by the same way with the example 1 to obtain the titled compound.

yield: 54%

Example 56
1-[(5-ethyl-2-methoxy-6-methylpyridin-3-yl)aminocarbonyl]-4-(2-hydroxy-6-methylphenyl)piperazine Phenyl-N-(5-ethyl-2-methoxy-6-methylpyridin-3-yl)carbamate and 1-(2-hydroxy-6-methylphenyl)piperazine were reacted by the same way with the example 1 to obtain the titled compound.

yield: 57%

Example 57
1|(5-ethyl-2-methoxy-6-methylpyridin-3-yl)aminocarbonyl|-4-(2-hydroxy-4-methylphenyl)piperazine Phenyl-N-(5-ethyl-2-methoxy-6-methylpyridin-3-yl)carbamate and 1-(2-hydroxy-4-methylphenyl)piperazine were reacted by the same way with example 1 to obtain the titled compound.

yield: 52%

Example 58
1-|(5-ethyl-2-methoxy-6-methylpyridin-3-yl)aminocarbonyl|-4-(5-chloro-2-methylphenyl)piperazine Phenyl-N-(5-ethyl-2-methoxy-6-methylpyridin-3-yl)carbamate and 1-(5-chloro-2-methylphenyl)piperazine were reacted by the same way with the example 1 to obtain the titled compound.

yield: 63%

Example 59
1-|(5-ethyl-2-methoxy-6-methylpyridin-3-yl)aminocarbonyl|-4-(3-chloro-4-fluorophenyl)piperazine Phenyl-N-(5-ethyl-2-methoxy-6-methylpyridin-3-yl)carbamate and 1-(3-fluorophenyl)piperazine were reacted by the same way with the example 1 to obtain the titled compound.

yield: 65%

Example 60
1-|(5-ethyl-2-methoxy-6-methylpyridin-3-yl)aminocarbonyl|-4-(2-methoxyphenyl)piperazine Phenyl-N-(5-ethyl-2-methoxy-6-methylpyridin-3-yl)carbamate and 1-(2-methoxyphenyl)piperazine were reacted by the same way with the example 1 to obtain the titled compound.

yield: 69%

Example 61
1-|(5-ethyl-2-methoxy-6-methylpyridin-3-yl)aminocarbonyl|-4-(2-chlorophenyl)piperazine Phenyl-N-(5-ethyl-2-methoxy-6-methylpyridin-3-yl)carbamate and 1-(2-chlorophenyl)piperazine were reacted by the same way with the example 1 to obtain the titled compound.

yield: 72%

Example 62
1-|(5-ethyl-2-methoxy-6-methylpyridin-3-yl)methylaminocarbonyl|-4-(4-fluorophenyl)piperazine Phenyl-N-(5-ethyl-2-methoxy-6-methylpyridin-3-yl)carbamate and 1-(4-fluorophenyl)piperazine were reacted by the same way with the example 1 to obtain the titled compound.

yield: 63%

Example 63
1-|(5-ethyl-2-methoxy-6-methylpyridin-3-yl)methylaminocarbonyl|-4-(3-chlorophenyl)piperazine Phenyl-N-(5-ethyl-2-methoxy-6-methylpyridin-3-yl)carbamate and 1-(3-chlorophenyl)piperazine were reacted by the same way with the example 1 to obtain the titled compound.

yield: 68%

Example 64
1-{|(5-ethyl-2-methoxy-6-methylpyridin-3-yl|ethylaminocarbonyl}-4-(4-fluorophenyl)piperazine Phenyl-N-|2-(5-ethyl-2-methoxy-6-methylpyridin-3-yl)ethyl|carbamate and 1-(4-fluorophenyl)piperazine were reacted by the same way with the example 1 to obtain the titled compound.

yield: 65%

Example 65
1-{|2-(5-ethyl-2-methoxy-6-methylpyridin-3-yl)ethyl|aminocarbonyl}-4-(2-methoxyphenyl)piperazine Phenyl-N-(5-ethyl-2-methoxy-6-methylpyridin-3-yl)carbamate and 1-(2-methoxyphenyl)piperazine were reacted by the same way with the example 1 to obtain the titled compound.

yield: 63%

Example 66
1-{|3-(5-ethyl-2-methoxy-6-methylpyridin-3-yl)propyl|aminocarbonyl}-4-(2-methoxyphenyl)piperazine Phenyl-N-|3-(5-ethyl-2-methoxy-6-methylpyridin-3-yl)propyl|carbamate and 1-(2-methoxyphenyl)piperazine were reacted by the same way with the example 1 to obtain the titled compound.

yield: 67%

Example 67
1-{|(5-(5-ethyl-2-methoxy-6-methylpyridin-3-yl)pentyl|aminocarbonyl}-4-(2-methoxyphenyl)piperazine Phenyl-N-|5-(5-ethyl-2-methoxy-6-methylpyridin-3-yl)pentyl|carbamate and 1-(2-methoxyphenyl)piperazine were reacted by the same way with the example 1 to obtain the titled compound.

yield: 52%

Example 68
1-{|6-(5-ethyl-2-methoxy-6-methylpyridin-3-yl)heptyl|aminocarbonyl-}-4-(2-methoxyphenyl)piperazine Phenyl-N-|6-(5-ethyl-2-methoxy-6-methylpyridin-3-yl)heptyl|carbamate and 1-(2-methoxyphenyl)piperazine were reacted by the same way with the example 1 to obtain the titled compound.

yield: 49%

Example 69
1-|(5-ethyl-2-methoxy-6-methylpyridin3-yl)aminocarbonyl|methyl-4-(2-methoxyphenyl)piperazine a) N-(5-ethyl-2-methoxy-6-methylpyridin-3-yl)chloroacetamide:

After chloroacetic acid (1.35 g, 14.3 mmol) were dissolved into 20 ml of tetrahydrofuran, added 1,1-carbonyldiimidazole(2.32 g, 14.3 mmol), stirred at room temperature for 1 hour, 3-amino-5-ethyl-2-methoxy-6-methylpyridine (2.0 g, 13.0 mmol) were added. After the reaction mixture were stirred for 2 hours, the mixture of reaction were concentrated, purified by column chromatography to obtain 2.20 g of the titled compound.

yield: 73.3%; $^1$H-NMR(500 MHz, CDCl$_3$); δ1.17(3H,t), 2.39(5H,m), 3.99(3H,s), 4.17(2H,s), 8.62(1H,s)

b) 1-[(5-ethyl-2-methoxy-6-methylpyridine-3-yl)aminocarbonyl|methyl-4-(2-methoxyphenyl)piperazine After N-(5-ethyl-2-methoxy-6-metylpyridine-3-yl)chloroacetamide(0.10 g, 0.43 mmol) and 1-(2-methoxyphenyl)piperazine(0.0091 g, 0.47 mmol) were dissolved into tetrahydrofuran(5 ml) and was added DBU (0.060 g, 0.43 mmol), the reaction mixtures were stirred at room temperature for 2 hours. After the product of reaction were concentrated, separated by column chromatography to obtain 0.12 g of the titled compound.

yield: 70%

Example 70

1-|(5-ethyl-2-methoxy-6-methylpyridine-3-yl) aminocarbonyl|methyl-4-(3-chlorophenyl)piperazine N-(5-ethyl-2-methoxy-6-methylpyridine-3-yl) chloroacetamide and 1-(3-chlorophenyl)piperazine were reacted by the same way with the example 69 to obtain the titled compound.

yield: 68%

Example 71

1-|(5-ethyl-2-methoxy-6-methylpyridine-3-yl) aminocarbonyl|methyl-4-(2-fluorophenyl)piperazine N-(5-ethyl-2-methoxy-6-methylpyridin-3-yl) chloroacetamide and 1-(3-fluorophenyl)piperazine were reacted by the same way with the example 69 to obtain the titled compound.

yield: 68%

Example 72

1|(5-ethyl-2-methoxy-6-methylpyridin-3-yl) aminocarbonyl|-4-benzylpiperazine a) 1-|(5-ethyl-2-methoxy-6-methylpyridin-3-yl) aminocarhonyl|-4-(4-methoxbenzyl)piperazine.

After 3-amino-5-ethyl-2-methoxy-6-methylpyridine(1.06 g, 6.35 mmol) was dissolved in 20 ml of tetrahydrofuran, 1,1-carbonyldiimidazole(1.08 g, 6.67 mmol) was added thereto. The mixture of reaction was stirred at room temperature for half hour and then benzylpiperazine(1.12 g, 6.35 mmol) was added. After the reaction mixture was stirred for 2 hours, the reaction mixture was concentrated and chromatographed to obtain 1.78 g of the oil phase of the titled compound.

yield: 76%; $^1$H-NMR(500 MHz.CDCl$_3$): δ1.16(3H,t), 2.36(3H,s), 2.48(4H,t), 3.42(4H,s), 3.54(2H,t), 3.95(H,s), 7.31(5H,s), 8.19(1H,s)

b) 1-(5-ethyl-2-methoxy-6-methylpyridin-3-yl) aminocarbonyl piperazine

After 1-[(5-ethyl-2-methoxy-6-methylpyridin-3-yl) aminocarbonyl]-4-benzyl piperazine (1.71 g, 4.61 mmol) was added the solution of 30 ml of ethanol and 10 ml of glacial acetic acid in the presence of 5% Pd/C, the reaction mixture were stirred under hydrogen gas(40 psi) for 4 hours and extracted with dichloromethane. The mixture was dried with anhydrous magnesium sulfate, filtrated, concentrated and chromatographed to obtain 1.2 g of white solid of the titled compound.

yield: 93%; $^1$H-NMR(500 MHz, CDCl$_3$): δ1.16(3H,s), 2.35(3H,s), 2.48(2H,q), 2.94(4H,t), 3.52(4H,t), 8.02(1H,s)

c) 1-|(5-ethyl-2-methoxy-6-methylpyridin-3-yl) aminocarboniyl|-4-benzylpiperazine After 1-(5-ethyl-2-methoxy-6-methylpyridin-3-yl) aminocarbonyl piperazine (0.16 g, 0.57 mmol) and benzylchloride(0.076 g, 0.60 mmol) were added in DMF 5 ml in the presence of NaHCO$_3$(0.114 g, 1.36 mmol), the reaction mixtures were stirred in 90° C. for 4 hours. The reaction solution was cooled at room temperature and the reaction mixture was extracted with dichloromethane and chromatographed to obtain 0.082 gm of the titled compound.

yield: 39%; $^1$H-NMR(500 MHz, CDCl$_3$) δ1.16(3H,t), 2.36(3H,s), 2.48(4H,t), 3.42(4H,t) 3.54(2H,s), 3.95(5H,s), 7.31(5H,s), 8.19(1H,s)

Example 73

1-|(5-ethyl-2-methoxy-6-methylpyridin-3-yl) aminocarbonyl|-4-(4-methoxybenzyl)piperazine 1-(5-ethyl-2-methoxy-6-methylpyridin-3-yl) aminocarbonylpiperazine and 4-methoxybenzylchloride were reacted by the same way with the example 72 to obtain the titled compound.

yield: 42%

Example 74

1-|(5-ethyl-2-methoxy-6-methylpyridin-3-yl) aminocarbonyl|4-(2-methoxybenzyl)piperazine 1-(5-ethyl-2-methoxy-6-methylpyridin-3-yl)aminocarbonylpipeazine and 2-methoxybenzylchloride were reacted by the same way with the example 72 to obtain the titled compound.

yield: 47%

Example 75

1-|(5-ethyl-2-methoxy-6-methylpyridin-3-yl) aminocarbonyl|-4-(4-fluorobenzyl)piperazine 1-(5-ethyl-2-methoxy-6-methylpyridin-3-yl) aminocarbonylpipeazine and 4-fluorobenzylchloride were reacted by the same way with the example 72 to obtain the titled compound.

yield: 52%

Example 76

1-|(2-ethoxy-5-ethyl-6-methylpyridin-3-yl)aminocarbonyl|-4-(2-methoxyphenyl)piperazine Phenyl-N-(2-ethoxy-5-ethyl-6-methylpyridin-3-yl) carbamate and 1-(2-methoxyphenyl)piperazine were reacted by the same way with the example 1 to obtain the titled compound.

yield: 82%

Example 77

1-|(2-ethoxy-5-ethyl-6-methylpyridin-3-yl)aminocarbonyl|-4-(2-fluorophenyl)piperazine Phenyl-N-(2-ethoxy-5-ethyl-6-methylpyridin-3-yl) carbamate and 1-(2-fluorophenyl)piperazine were reacted by the same way with the example 1 to obtain the titled compound.

yield: 87%

Example 78

1-|(2-ethoxy-5-ethyl-6-methylpyridin-3-yl)aminocarbonyl|-4-(3-chlorophenyl) piperazine Phenyl-N-(2-ethoxy-5-ethyl-6-methylpyridin-3-yl) carbamate and 1-(3-chlorophenyl)piperazine were reacted by the same way with the example 1 to obtain the titled compound.

yield: 83%

Example 79

1-|(2-ethoxy-5-ethyl-6-methylpyridin-3-yl)aminocarbonyl|-4-(2-ethoxyphenyl) piperazin:

Phenyl-N-(2-ethoxy-5-ethyl-6-methylpyridin-3-yl) carbamate and 1-(2-ethoxyphenyl)piperazine were reacted by the same way with the example 1 to obtain the titled compound.

yield: 79%

Example 80

1-|(5-ethyl-6-methyl-2-phenoxypyridin-3-yl) aminocarbonyl|-4-(2-methoxyphenyl)piperazine Phenyl-N-(5-ethyl-6-methyl-2-phenoxypyridin-3-yl) carbamate and 1-(2-methoxyphenyl)piperazine were reacted by the same way with the example 1 to obtain the titled compound.

yield: 88%

Example 81
1-|(5-ethyl-6-methyl-2-phenoxypyridin-3-yl)aminocarbonyl|-4-(3-chlorophenyl)piperazine Phenyl-N-(5-ethyl-6-methyl-2-phenoxypyridin-3-yl) carbamate and 1-(3-chlorophenyl)piperazine were reacted by the same way with the example 1 to obtain the titled compound.

yield: 85%

Example 82
1-|(5-ethyl-6-methyl-2-phenoxypyridin-3-yl)aminocarbonyl|-4-(3-acetoxyphenyl)piperazine Phenyl-N-(5-ethyl-6-methyl-2-phenoxypyridin-3-yl) carbamate and 1-(3-acetoxyphenyl)piperazine were reacted by the same way with the example 1 to obtain the titled compound.

yield: 83%

Example 83
1-|(5-ethyl-6-methyl-2-phenoxypyridin-3-yl)aminocarbonyl|-4-(2-fluorophenyl)piperazine Phenyl-N-(5-ethyl-6-methyl-2-phenoxypyridin-3-yl) carbamate and 1-(2-fluorophenyl)piperazine were reacted by the same way with the example 1 to obtain the titled compound.

yield: 72%

Example 84
1-|(5-ethyl-6-methyl-2-phenoxypyridin-3-yl)aminocarbonyl|-4-(3,5-xylyl)piperazine Phenyl-N-(5-ethyl-6-methyl-2-phenoxypyridin-3-yl) carbamate and 1-(3,5-xylyl)piperazine were reacted by the same way with the example 1 to obtain the titled compound.

yield: 78%

Example 85
1-|(5-ethyl-6-methyl-2-phenoxypyridin-3-yl)aminocarbonyl|-4-(3,5-dimethoxyphenyl)piperazine Phenyl-N-(5-ethyl-6-methyl-2-phenoxypyridin-3-yl) carbamate and 1-(3,5-dimethoxyphenyl)piperazine were reacted by the same way with the example 1 to obtain the titled compound.

yield: 75%

Example 86
1-|(5-ethyl-6-methyl-2-phenoxypyridin-3-yl)aminocarbonyl|-4-(3,5-dichlorophenyl)piperazine Phenyl-N-(5-ethyl-6-methyl-2-phenoxypyridin-3-yl) carbamate and 1-(3,5-dichlorophenyl)piperazine were reacted by the same way with the example 1 to obtain the titled compound.

yield: 82%

Example 87
1-|(5-ethyl-6-methyl-2-phenoxypyridin-3-yl)aminocarbonyl|-4-(3-hydroxy-4-methoxyphenyl)piperazine Phenyl-N-(5-ethyl-6-methyl-2-phenoxypyridin-3-yl) carbamate and 1-(3-hydroxy-4-methoxyphenyl)piperazine were reacted by the same way with the example 1 to obtain the titled compound.

yield: 69%

Example 88
1-|(5-ethyl-6-methyl-2-phenoxypyridin-3-yl)aminocarbonyl|-4-(3-hydroxyphenyl)piperazine Phenyl-N-(5-ethyl-6-methyl-2-phenoxypyridin-3-yl) carbamate and 1-(3-hydroxyphenyl)piperazine were reacted by the same way with the example 1 to obtain the titled compound.

yield: 72%

Example 89
1-|(5-ethyl-6-methyl-2-methylaminopyridin-3-yl)aminocarbonyl|-4-(2-methoxyphenyl)piperazine Phenyl-N-(5-ethyl-6-methyl-2-methylaminopyridin-3-yl) carbamate and 1-(2-methoxyphenyl)piperazine were reacted by the same way with the example 1 to obtain the titled compound.

yield: 73%

Example 90
1-|(5-ethyl-6-methyl-2-methylaminopyridin-3-yl)aminocarbonyl|-4-(3,5-dimethoxyphenyl)piperazine Phenyl-N-(5-ethyl-6-methyl-2-methylaminopyridin-3-yl) carbamate and 1-(3,5-dimetoxyphenyl)piperazine were reacted by the same way with the example 1 to obtain the titled compound.

yield: 82%

Example 91
1-|(5-ethyl-6-methyl-2-phenoxypyridin-3-yl)aminocarbonyl|-4-(3-chlorophenyl)piperazine Phenyl-N-(5-ethyl-6-methyl-2-methylaminopyridin-3-yl) carbamate and 1-(3-chlorophenyl)piperazine were reacted by the same way with the example 1 to obtain the titled compound.

yield: 79%

Example 92
1-|(5-ethyl-6-methylpyridin-3-yl)aminocarbonyl|-4-(2-methoxyphenyl)piperazine Phenyl-N-(5-ethyl-6-methylpyridin-3-yl)carbamate and 1-(2-methoxyphenyl)piperazine were reacted by the same way with the example 1 to obtain the titled compound.

yield: 80%

Example 93
1-|(5-ethyl-6-methylpyridin-3-yl)aminocarbonyl|-4-(3,5-dimethoxyphenyl)piperazine Phenyl-N-(5-ethyl-6-methylpyridin-3-yl)carbamate and 1-(3,5-dimethoxyphenyl)piperazine were reacted by the same way with the example 1 to obtain the titled compound.

yield: 85%

Example 94
1-{|5-ethyl-6-methyl-2-(-piperazinyl)pyridin-3-yl|aminocarbonyl}-4-(3-chlorophenyl)piperazine Phenyl-N-{|5-ethyl-6-methyl-2-(1-piperazinyl)pyridin-3-yl|carbamate and 4-(3-chlorophenyl)piperazine were reacted by the same way with the example 1 to obtain the titled compound.

yield: 87%

Example 95
1-{|5-ethyl-6-methyl-2-(4-boc-piperazinyl)pyridin-3-yl|aminocarbonyl}-4-(3-chlorophenyl)piperazine Phenyl-N-{|5-ethyl-6-methyl-2-(4-bocpiperazinyl)pyridin-3-yl|carbamate and 1-(3-chlorophenyl)piperazine were reacted by the same way with the example 1 to obtain the titled compound.

yield: 92%

Example 96
1-{|5-ethyl-6-methyl-2-(4-boc-piperazinyl)pyridin-3-yl|-aminocarbonyl}-4-(2-methoxyphenyl)piperazine Phenyl-N-{|5-ethyl-6-methyl-2-(4-boc-piperazinyl) pyridin-3-yl|carbamate and 1-(2-methoxyphenyl)piperazine were reacted by the same way with the example 1 to obtain the titled compound. yield: 94%

Example 97
1-|(5-ethyl-2-methoxy-6-methylpyridin-3-yl)aminothiocarbonyl|-4-(2-methoxyphenyl)piperazine Phenyl-N-(5-ethyl-2-methoxy-6-methylpyridin-3-yl) thiocarbamate and 1-(2-methoxyphenyl)piperazine were reacted by the same way with the example 1 to obtain the titled compound.
yield: 93%

Example 98
1-|(5-ethyl-2-methoxy-6-methylpyridin-3-yl)aminothiocarbonyl|-4-(3-chlorophenyl)piperazine Phenyl-N-(5-ethyl-2-methoxy-6-methylpyridin-3-yl) thiocarbamate and 1-(3-chlorophenyl)piperazine were reacted by the same way with the example 1 to obtain the titled compound.
yield: 88%

Example 99
1-|(5-ethyl-2-methoxy-6-methylpyridin-3-yl)aminothiocarbonyl|-4-(2-fluorophenyl)piperazine Phenyl-N-(5-ethyl-2-methoxy-6-methylpyridin-3-yl) thiocarbamate and 1-(2-fluorophenyl)piperazine were reacted by the same way with the example 1 to obtain the titled compound.
yield: 82%

Example 100
1-|(5-ethyl-2-methoxy-6-methylpyridin-3-yl)aminothiocarbonyl|-4-(3,5-dimethoxyphenyl)piperazine Phenyl-N-(5-ethyl-2-methoxy-6-methylpyridine-3-yl) thiocarbamate and 1-(3,5-dimethoxyphenyl)piperazine were reacted by the same way with the example 1 to obtain the titled compound.
yield: 85%

Example 101
1-|(5-ethyl-2-methoxy-6-methylpyridin-3-yl)aminothiocarbonyl|-4-(3,5-dichlorophenyl)piperazine Phenyl-N-(5-ethyl-2-methoxy-6-methylpyridin-3-yl) thiocarbamate and 1-(3,5-dichlorophenyl)piperazine were reacted by the same way with the example 1 to obtain the titled compound.
yield: 84%

Example 102
1-[(5-ethyl-2-methoxy-6-methylpyridin-3-yl)oxycarbonyl]-4-(2-methoxyphenyl)piperazine Phenyl-(5-ethyl-2-methoxy-6-methylpyridin-3-yl) carbonate and 1-(2-methoxyphenyl)piperazine were reacted by the same way with the example 1 to obtain the titled compound.
yield: 72%

Example 103
1-|(5-ethyl-2-methoxy-6-methylpyridin-3-yl)oxycarbonyl|-4-(3-chlorophenyl)piperzine:

Phenyl-(5-ethyl-2-methoxy-6-methylpyridin-3-yl) carbonate and 1-(3-chlorophenyl)piperazine were reacted by the same way with the example 1 to obtain the titled compound.
yield: 74%

Example 104
1-|(5-ethyl-2-methoxy-6-methylpyridin-3-yl)oxycarbonyl|-4-(3,5-dimethoxyphenyl)piperazine Phenyl-(5-ethyl-2-methoxy-6-methylpyridin-3-yl) carbonate and 1-(3,5-dimethoxyphenyl)piperazine were reacted by the same way with the example 1 to obtain the titled compound.
yield: 77%

Example 105
1-|(5-ethyl-2-methoxy-6-methylpyridin-3-yl)methyloxycarbonyl|-4-(2-methoxyphenyl)piperazine Phenyl-(5-ethyl-2-methoxy-6-methylpyridin-3-yl) methylcarbonate and 1-(2-methoxyphenyl)piperazine were reacted by the same way with the example 1 to obtain the titled compound.
yield: 82%

Example 106
1-|(5-ethyl-2-methoxy-6-methylpyridin-3-yl)methyloxycarbonyl|-4-(3-chlorophenyl-1)piperazine Phenyl-(5-ethyl-2-methoxy-6-methylpyridin-3-yl) methylcarbonate and 1-(3-chlorophenyl)piperazine were reacted by the same way with the example 1 to obtain the titled compound.
yield: 79%

Example 107
1-|(5,6-dimethyl-2-methoxypyridin-3-yl)aminocarbonyl|-4-phenylpiperazine Phenyl-N-(5,6-dimethyl-1-methoxypyridin-3-yl) carbamate and 1-phenylpiperazine were reacted by the same way with the example 1 to obtain the titled compound.
yield: 84%

Example 108
1-|(5,6-dimethyl-2-methoxypyridin-3-yl)aminocarboniyl|-4-methoxyphenyl)piperazine Phenyl-N-(5,6-dimethyl-2-methoxypyridin-3-yl) carbamate and 1-(2-methoxyphenyl)piperazine were reacted by the same way with the example 1 to obtain the titled compound.
yield: 8%

Example 109
1-|(5,6-dimethyl-2-methoxypyridin-3-yl)aminocarbonyl]-4-(3-chlorophenyl)piperazine Phenyl-N-(5,6-dimethyl-2-methoxypyridin-3-yl) carbamate and 1-(3-chlorophenyl)piperazine were reacted by the same way with the example 1 to obtain the titled compound.
yield: 92%

Example 110
1-|(5,6-dimethyl-2-methoxypyridin-3-yl)aminocarbonyl|-4-fluorophenyl)piperazine Phenyl-N-(5,6-dimethyl-2-methoxypyridin-3-yl) carbamate and 1-(2-fluorophenyl)piperazine were reacted by the same way with the example 1 to obtain the titled compound.
yield: 79%

Example 111
1-|(5,6-dimethyl-2-methoxypyridin-3-yl)aminocarbonyl|-4-(3,5-difluorophenyl)piperazine Phenyl-N-(5,6-dimethyl-2-methoxypyridin-3-yl) carbamate and 1-(3,5-difluorophenyl)piperazine were reacted by the same way with the example 1 to obtain the titled compound.
yield: 87%

Example 112
1-[(5,6-dimethyl-2-methoxypyridin-3-yl)aminothiocarbonyl]-4-(2-hydroxyphenyl)piperazine Phenyl-N-(5,6-dimethyl-2-methoxypyridin-3-yl) carbamate and 1-(2-hydroxyphenyl)piperazine were reacted by the same way with the example 1 to obtain the titled compound.

Example 113
1-[(5,6-dimethyl-2-methoxypyridin-3-yl)]-4-(3-hydroxyphenyl)piperazine Phenyl-N-(5,6-dimethyl-2-methoxypyridin-3-yl) carbamate and 1-(3-hydroxyphenyl)piperazine were reacted by the same way with the example 1 to obtain the titled compound.
yield 78%

Example 114
1-[(5,6-dimethyl-2-methoxypyridin-3-yl)aminocarbonyl]-4-(4-hydroxyphenyl) piperazine Phenyl-N-(5,6-dimethyl-2-methoxypyridin-3-yl) carbamate and 1-(4-hydroxyphenyl)piperazine were reacted by the same way with the example 1 to obtain the titled compound.
yield: 72%

Example 115
1-[(5,6-dimethyl-2-methoxypyridin-3-yl)aminocarbonyl]-4-(3-acetoxyphenyl)piperazine Phenyl N (5,6-dimethyl-2-methoxypyridin-3-yl) carbamate and 1-(3-acetylphenyl)piperazine were reacted by the same way with the example 1 to obtain the titled compound.
yield 92%

Example 116
1-[(5,6-dimethyl-2-methoxypyridin-3-yl)aminocarbonyl]-4-(4-acetoxyphenyl) piperazine Phenyl-N-(5,6-dimethyl 2methoxypyridin 3-yl)carbamate and 1-(4-acetoxyphenyl)piperazine were reacted by the same way with the example 1 to obtain the titled compound.
yield: 89%

Example 117
1-[(5,6-dimethyl-2-methoxypyridin-3-yl)aminocarbonyl]-4-(3-acethoxy-4-methoxyphenyl)piperazine Phenyl N (5,6-dimethyl-2-methoxypyridine 3-yl) carbamate and 1-(3-acetoxy-4-methoxyphenyl)piperazine were reacted by the same way with the example 1 to obtain the titled compound.
yield: 69%

Example 118
1-[(5,6-dimethyl-2-methoxypyridin-3-yl)aminocarbonyl]-4-(3,5-dimethoxyphenyl)piperazine Phenyl-N-(5,6-dimethyl-2-methoxypyridin-3-yl) carbamate and 1-(3,5-dimethoxyphenyl)piperazine were reacted by the same way with the example 1 to obtain the titled compound.
yield: 88%

Example 119
1-[(5,6-dimethyl-2-methoxypyridin-3-yl)aminocarbonyl]-4-(2,3-xylyl)piperazine Phenyl-N-(5,6-dimethyl-2-methoxypyridin-3-yl) carbamate and 1-(2,3-xylyl)piperazine were reacted by the same way with the example 1 to obtain the titled compound.
yield: 72%

Example 120
1-[(5,6-dimethyl-2-methoxypyridin-3-yl)aminocarbonyl]-4-(3,5-xylyl)piperazine Phenyl-N-(5,6-dimethyl-2-methoxypyridin-3-yl) carbamate and 1-(3,5-xylyl)piperazine were reacted by the same way with the example 1 to obtain the titled compound.
yield: 68%

Example 121
1-[(5,6-dimethyl-2-methoxypyridin-3-yl)aminocarbonyl]-4-(2,5-xylyl)piperazine Phenyl-N-(5,6-dimethyl-2-methoxypyridin-3-yl) carbamate and 1-(2,5-xylyl)piperazine were reacted by the same way with the example 1 to obtain the titled compound.
yield: 72%

Example 122
1-[(5,6-dimethyl-2-methoxypyridin-3-yl)aminocarbonyl]-4-(2-hydroxy-4-methylphenyl)piperazine Phenyl-N-(5,6-dimethyl-2-methoxypyridin-3-yl) carbamate and 1-(2-hydroxy-4-methylphenyl)piperazine were reacted by the same way with the example 1 to obtain the titled compound.
yield: 77%

Example 123
1-[(5,6-dimethyl-2-methoxypyridin-3-yl)aminocarbonyl]-4-(3-hydroxy-4-methoxyphenyl)piperazine Phenyl-N-(5,6-dimethyl-2-methoxypyridin-3-yl) carbamate and 1-(3-hydroxy-4-methoxyphenyl)piperazine were reacted by the same way with the example 1 to obtain the titled compound.
yield: 69%

Example 124
1[(5,6-dimethyl-2-methoxypyridin-3-yl)aminocarbonyl]-4-(1-naphthyl)piperazine Phenyl-N-(5,6-dimethyl-2-methoxypyridin-3-yl) carbamate and 1-(1-naphthyl)piperazine were reacted by the same way with the example 1 to obtain the titled compound.
yield: 74%

Example 125
1-[(5,6-dimethyl-2-methoxypyridin-3-yl)aminocarbonyl]-4-(1-anthryl)piperazine Phenyl-N-(5,6-dimethyl-2-methoxypyridin-3-yl) carbamate and 1-(1-anthryl)piperazine were reacted by the same way with the example 1 to obtain the titled compound.
yield: 62%

Example 126
1-[(5,6-dimethyl-2-methoxypyridin-3-yl)aminothiocarbonyl]-4-(3-chlorophenyl) piperazine Phenyl-N-(5,6-dimethyl-2-methoxypyridin-3-yl) thiocarbamate and 1-(3-chlorophenyl)piperazine were reacted by the same way with the example 1 to obtain the titled compound.
yield: 69%

Example 127
1-[(5,6-dimethyl-2-methoxypyridin-3-yl)aminocarbonyl]-4-(3,5-dichlorophenyl) piperazine Phenyl-N-(5,6-dimethyl-2-methoxypyridin-3-yl) thiocarbamate and 1-(3,5-dichlorophenyl)piperazine were reacted by the same way with the example 1 to obtain the titled compound.
yield: 82%

Example 128
1-[(5,6-dimethyl-2-methoxypyridin-3-yl)aminocarbonyl]-4-(2-methoxyphenyl) piperazine Phenyl-N-(5,6-dimethyl-2-methoxypyridin-3-yl) thiocarbamate and 1-(2-methoxyphenyl)piperazine were reacted by the same way with the example 1 to obtain the titled compound.

yield: 70%

Example 129
1-[(5,6-dimethyl-2-methoxypyridin-3-yl)aminothiocarbonyl]-4-(3,5-dimethoxyphenyl)piperazine Phenyl-N-(5,6-dimethyl-2-methoxypyridin-3-yl) thiocarbamate and 1-(3,5-dimethoxyphenyl)piperazine were reacted by the same way with the example 1 to obtain the titled compound.

yield: 69%

Example 130
1-[(2-methoxy-5,6,7-trihydro-1-pyrinden-3-yl)aminocarbonyl]-4-(2-methoxyphenyl)piperazine Phenyl-N-(2-methoxy-5,6,7-trihydro-1-pyrinden-3-yl)carbamate and 1-(2-methoxyphenyl)piperazine were reacted by the same way with the example 1 to obtain the titled compound.

yield: 64%

Example 131
1-[(2-methoxy-5,6,7-trihydro-1-pyrinden-3-yl)aminocarbonyl]-4-(3-chlorophenyl)piperazine Phenyl-N-(2-methoxy-5,6,7-trihydro 1-pyrinden-3-yl)carbamate and 1-(3-chlorophenyl)piperazine were reacted by the same way with the example 1 to obtain the titled compound.

yield: 63%

Example 132
1-[(2-methoxy-5,6,7-trihydro-1-pyrinden-3-yl)aminocarbonyl]-4-(2-fluorophenyl)piperazine Phenyl-N-(2-methoxy-5,6,7-trihydro-1-pyrinden-3-yl)carbamate and 1-(2-fluorophenyl)piperazine were reacted by the same way with the example 1 to obtain the titled compound.

yield: 59%

Example 133
1-[(2-methoxy-5,6,7,8-tetrahydroisoquinolin-3-yl)aminocarbonyl]-4-(2-methoxyphenyl)piperazine Phenyl-N-(2-methoxy-5,6,7,8-tetrahydroisoquinolin-3-yl)carbamate and 1-(2-methoxyphenyl)piperazine were reacted by the same way with the example 1 to obtain the titled compound.

yield: 64%

Example 134
1-[(2-methoxy-5,6,7,8-tetrahydroisoquinolin-3-yl)aminocarbonyl]-4-(3-chlorophenyl)piperazine Phenyl-N-(2-methoxy-5,6,7,8-tetrahydroisoquinolin-3-yl)carbamate and 1-(3-chlorophenyl)piperazine were reacted by the same way with the example 1 to obtain the titled compound.

yield: 69%

Example 135
1-[(2-methoxy-5,6,7,8-tetrahydroisoquinolin-3-yl)aminocarbonyl]-4-(2-fluorophenyl)piperazine Phenyl-N-(2-methoxy-5,6,7,8-tetrahydroisoquinolin-3-yl)carbamate and 1-(2-fluorophenyl)piperazine were reacted by the same way with the example 1 to obtain the titled compound.

yield: 70%

Example 136
1-[(5-isopropyl-2-methoxy-6-methylpyridin-3-yl)aminocarbonyl]-4-(2-methoxyphenyl)piperazine Phenyl-N-(5-isopropyl-2-methoxy-6-methylpyridin-3-yl)carbamate and 1-(2-methoxyphenyl)piperazine were reacted by the same way with the example 1 to obtain the titled compound.

yield: 64%

Example 137
1-[(5-isopropyl-2-methoxy-6-methylpyridin-3-yl)aminocarbonyl]-4-(3-chlorophenyl)piperazine Phenyl-N-(5-isopropyl-2-methoxy-6-methylpyridine-3-yl)carbamate and 1-(3-chlorophenyl)piperazine were reacted by the same way with the example 1 to obtain the titled compound.

yield: 63%

Example 138
1-[(5-isopropyl-2-methoxy-6-methylpyridin-3-yl)aminocarbonyl]-4-(2-fluorophenyl)piperazine Phenyl-N-(5-isopropyl-2-methoxy-6-methylpyridin-3-yl)carbamate and 1-(2-fluorophenyl)piperazine were reacted by the same way with the example 1 to obtain the titled compound.

yield: 59%

Example 139
1-[(2-methoxypyridin-3-yl)aminocarbonyl]-4-phenylpiperazine

Phenyl-N-(2-methoxypyridin-3-yl)carbamate and 1-phenylpiperazine were reacted by the same way with the example 1 to obtain the titled compound.

yield: 88%

Example 140
1-[(2-methoxypyridin-3-yl)aminocarbonyl]-4-(2-methoxyphenyl)piperazine Phenyl-N-(2-methoxypyridin-3-yl)carbamate and 1-(2-methoxyphenyl)piperazine were reacted by the same way with the example 1 to obtain the titled compound.

yield: 86%

Example 141
1-[(2-methoxypyridin-3-yl)aminocarbonyl]-4-(4-methoxyphenyl)piperazine Phenyl-N-(2-methoxypyridin-3-yl)carbamate and 1-(4-methoxyphenyl)piperazine were reacted by the same way with the example 1 to obtain the titled compound.

yield: 85%

Example 142
1-[(2-methoxypyridin-3-yl)aminocarbonyl]-4-(3-chlorophenyl)piperazine Phenyl-N-(2-methoxypyridin-3-yl)carbamate and 1-(3-chlorophenyl)piperazine were reacted by the same way with the example 1 to obtain the titled compound.

yield: 72%

Example 143
1-[(5-ethyl-2-methoxy-6-methylpyridin-3-yl)aminocarbonyl]-4-[(3-propargylamino)pyridin-2-yl]piperazine Phenyl-N-(5-ethyl-2-methoxy-6-methylpyridin-3-yl)carbamate and 1-[(3-propargylamino)pyridine-2-yl)

piperazine were reacted by the same way with the example 1 to obtain the titled compound.
yield: 61%

Example 144
1-|(5-ethyl-2-methoxy-6-methylpyridin-3-yl) methylaminocarbonyl|-4-|(3-propargylamino)pyridin-2-yl| piperazine Phenyl-N-(5-ethyl-2-methoxy-6-methylpyridin-3-yl) methylcarbamate and 1-|(3-propargylamino)pyridin-2-yl| piperazine were reacted by the same way with the example 1 to obtain the titled compound.
yield: 74%

Example 145
1-{|5-ethyl-6-methyl-2(1H)-pyridinon-3-yl| methylaminocarbonyl}-4-|(3-propargylamino)pyridin-2-yl| piperazine Phenyl-N-|5-ethyl-6-methyl-2(1H)-pyridinon-3-yl| methylcarbamate and 1-|(3-propargylamino)pyridin-2-yl| piperazine were reacted by the same way with the example 1 to obtain the titled compound.
yield: 77%

Example 146
1-{|5-ethyl-6-methyl-2(1H)-pyridinon-3-yl| methylaminocarbonyl}-4-|(3-dibenzylamino)pyridin-2-yl| piperazine Phenyl-N-|5-ethyl-6-methyl-2(1H)-pyridinon-3-yl| methylcarbamate and 1-|(3-dibenzylamino)pyridine-2-yl| piperazine were reacted by the same way with the example 1 to obtain the titled compound.
yield: 65%

Example 147
1-{|5-isopropyl-6-methyl-2(1H)-pyridinon-3-yl| methylaminocarbonyl}-4-|(3-ethylamino)pyridin-2-yl| piperazine Phenyl-N-|5-ethyl-6-methyl-2(1H)-pyridinon-3-yl| methylcarbamate and 1-|(3-ethylamino)pyridin-2-yl| piperazine were reacted by the same way with the example 1 to obtain the titled compound.
yield: 62%

Example 148
1-|(5-ethyl-2-methoxy-6-methylpyridin-3-yl) aminocarbonyl|-4-|(2-methoxyphenyl)piperazine-2-yl| piperazine salt of hydrochloride:

After 1-|(5-ethyl-2-methoxy-6-methylpyridin-3-yl) aminocarbonyl|-4-(2-methoxyphenyl)piperazine(5.0 g, 13 mmol) was dissolved in 400 ml of diethylether, the mixture was saturated by hydrogen chloride gas at 0° C. and stirred for 30 minutes and purified to obtain the titled compound.
yield: 98%

Example 149
1-|(5-ethyl-2-methoxy-6-methylpyridin-3-yl) aminocarbonyl|-4-(3-chlorophenyl)piperazine salt of hydrochloride:

1-|(5-ethyl-2-methoxy-6-methylpyridin-3-yl) aminocarbonyl|-4-(3-chlorophenyl)piperazine was reacted by the same way with the example 148 to obtain the titled compound.
yield: 98%

| example number | elementary analysis | $^1$H NMR (500 MHz, CDCl$_3$) δ | melting point |
| --- | --- | --- | --- |
| 1 | C$_{21}$H$_{28}$N$_4$O$_3$: theoretical, C, 65.60, H, 7.34, N, 14.57 experimental, C, 66.10, H, 7.25, N, 14.57 | 1.17 (3H,t, J = 7.5 Hz), 2.37 (3H, s), 2.55 (2H, q, J = 7.5 Hz), 3.11 (4H, t, J = 4.6 Hz), 3.69 (4H, t, J = 5.0 Hz), 3.88 (1H, s), 3.98 (3H, s), 6.89 (1H, s), 6, 94 (3H, m), 7.05 (1H, m), 8.21 (1H, s). | 115–118° C. |
| 2 | | 1.17 (3H, t, J = 7.5 Hz), 2.37 (3H, s), 2.55 (2H, q, J = 7.5 Hz), 3.26 (4H, t, J = 4.5 Hz), 3.68 (4H, t), 3.98 (3H, s), 6.91 (1H, s), 6.95 (4H, m), 7.28 (1H, m), 8.35 (1H, s). | 102–103° C. |
| 3 | | 1.17 (3H, t, J = 7.5 Hz), 2.37 (3H, s.), 2.55 (2H, q, J = 8.0 Hz), 3.12 (4H, t), 3.63 (4H, t), 3.78 (3H, s), 3.97 (3H, s), 6.85 (1H, s), 6.87 (2H, m), 6.97 (2H, m), 8.19 (1H, s). | 84–85° C. |
| 4 | | 1.17 (3H, t, J = 7.5 Hz), 2.37 (3H, s), 2.55 (2H, q, J = 7.5H z), 3.04 (4H, t), 3.68 (4H, t), 3.79 (3H, s), 3.86 (3H, s), 3.97 (3H, s), 6.43 (1H,d), 6.50 (1H, s), 6.87 (1H, d), 6.92 (1H, s), 8.21 (1H, s). | 116–119° C. |
| 5 | | 1.17 (3H, t, J = 7.5 Hz), 2.37 (3H, s), 2.55 (2H, q, J = 7.5 Hz), 3.14 (4H, t), 3.68 (4H, t), 3.85 (3H, s), 3.88 (3H, s), 3.97 (3H, s), 6.49 (1H, d), 6.60 (1H, s), 6.82 (1H, d), 6.92 (1H, s), 8.21 (1H, s). | 103–104° C. |
| 6 | C$_{22}$H$_{30}$N$_4$O$_4$: theoretical, C, 63.75, H, 7.30, N, 13.52 experimental C, 63.81, H, 7.31, N, 13.32 | 1.17 (2H, q, J = 7.5 Hz), 2.37 (3H, s), 2.55 (2H, q, J = 7.5 Hz), 3.27 (4H, t), 3.74 (4H, t), 3.79 (6H, s), 3.98 (3H, s), 6.09 (1H, s), 6.16 (2H, s), 6.90 (1H, s), 8.19 (1H, s) | 126–127° C. |
| 7 | | 1.16 (3H, t, J = 7.5 Hz), 2.37 (3H, s), 2.55 (2H, q, J = 7.5 Hz), 3.20 (4H, t, J = 4.7 Hz), 3.69 (4H, t), 3.80 (3H, s), 3.86 (6H, s), 3.98 (3H, s), 6.20 (2H, s), 8.19 (1H, s). | oil phase |
| 8 | C$_{22}$H$_{30}$N$_4$O$_3$: theoretical, C, 66.31, H, 7.59, N, 14.06 experimental | 1.17 (3H, q, J = 7.5 Hz), 1.48 (3H, t, J = 6.95 Hz), 2.37 (3H,s), 2,56 (2H, q, J = 7.5 Hz), 3.14 (4H, t, J = 4.7 Hz), 3.69(4H, t, J = 4.6 | 96–97° C. |

-continued

| example number | elementary analysis | $^1$H NMR (500 MHz, CDCl$_3$) δ | melting point |
|---|---|---|---|
| | C, 66.13, H, 7.72, N, 13.78 | Hz), 3.98 (3H, s), 4.10 (2H, q), 6.87 (1H, s), 6.92 (3H, m), 7.01 (1H, m), 8.21 (1H, s) | |
| 9 | | 1.16 (3H, t, J = 7.5 Hz), 2.36 (3H, s), 2.54 (2H, q, J = 7.5 Hz), 3.14 (4H, t), 3.45 (4H, t), 3.95 (3H, s), 6.83 (1H, s), 6.92 (2H, m), 7.03 (5H, m), 7.15 (1H, m), 7.31 (2H m), 8.16 (1H,s). | 167–168° C. |
| 10 | | 1.17 (3H, t, J = 7.5 Hz), 2.38 (3H, s), 2.55 (2H, q, J = 7.5 Hz), 3.27 (4H, t, J = 5.0 Hz), 3.70 (4H, t), 3.99 (3H, s), 6.55 (1H, d), 6.67 (1H, m), 6.91 (1H, m), 7.02 (2H, d), 7.11 (1H, m), 7.24 (2H, m), 7.34 (2H, m), 8.19 (1H, s). | oil phase |
| 11 | | 1.19 (3H, t, J = 7.5 Hz), 2.37 (3H, s), 2.55 (2H, q, J = 7.5 Hz), 3.14 (4H, t), 3.68 (4H, t), 3.97 (3H, s), 6.92 (1H, s), 6.94 (2H, m), 7.06 (2H, m), 8.20 (1H, s). | 120–121° C. |
| 12 | | 1.17 (3H, t, J = 7.5 Hz), 2.37 (3H, s), 2.55 (2H, q, J = 7.5 Hz), 3.16 (4H, t, J = 5.0 Hz), 3.66 (4H, t, J = 5.1 Hz), 3.98 (3H, s), 6.89 (1H, s), 6.91 (2H, m), 6.99 (2H, m), 8.19 (1H, s). | oil phase |
| 13 | C$_{20}$H$_{24}$N$_2$O$_2$F$_2$: theoretical C, 61.53, H, 6.20, N, 14.35 experimental, C, 61.31, H, 6.27, N, 14.04 | 1.17 (3H, t, J = 7.5 Hz), 2.38 (3H, s), 2.56 (2H, q), 3.29 (4H, t, J = 5.5 Hz), 3.68 (4H, t, J = 5.5 Hz), 3.99 (3H, s), 6.28 (1H, m), 6.32 (2H, d), 6.89 (1H, s), 8.18 (1H, s). | 115–116° C. |
| 14 | | 1.17 (3H, t, J = 7.5 Hz), 2.37 (3H, s), 2.56 (2H, q, J = 7.5 Hz), 3.31 (4H, t, J = 5.0 Hz), 3.69 (4H, t, J = 5.0 Hz), 3.98 (3H, s), 6.91 (1H, d), 7.09 (1H, d), 7.12 (2H, m), 7.39 (1H, m), 8.19 (1H, s). | 113–115° C. |
| 15 | | 1.19 (3H, t, J = 7.5 Hz), 2.38 (3H, s), 2.56 (2H, q, J = 7.0 Hz), 3.10 (4H, t, J = 5.0 Hz), 3.69 (4H, t, J = 5.0 Hz), 3.99 (3H, s), 6.82 (1H, d), 6.91 (1H, s), 7.04 (2H, m), 7.40 (1H, m), 8.22 (1H, s). | 97–99° C. |
| 16 | C$_{20}$H$_{25}$N$_4$O$_2$Cl$_1$: theoretical, C, 61.77, H, 6.48, N, 14.41 experimental, C, 61.79, H, 6.54, N, 14.26 | 1.17 (3H, t, J = 7.5 Hz), 2.38 (3H, s), 2.55 (2H, q, J = 7.5 Hz), 3.26 (4H, t, J = 5.0 Hz), 3.66 (4H, t, J = 5.0 Hz), 3.98 (3H, s), 6.79 (1H, d), 6.86 (1H, d), 6.89 (2H, d), 7.19 (1H, m), 8.18 (1H, m). | 104–105° C. |
| 17 | | 1.17 (3H, t, J = 7.5 Hz), 2.38 (3H, s), 2.51 (2H, q, J = 5.0 Hz), 3.48 (4H, t, J = 5.0 Hz), 3.75 (4H, t, J = 5.0 Hz), 3.98 (3H, s), 6.84 (3H, m), 8.35 (1H, s). | 74–75° C. |
| 18 | | 1.17 (3H, t, J = 7.5 Hz), 2.37 (3H, s), 2.54 (2H, q, J = 7.5 Hz), 3.26 (4H, t, J = 5.0 Hz), 3.77 (4H, t, J = 5.0 Hz), 3.98 (3H, s), 6.85 (1H, s), 6.97 (2H, m), 7.31 (1H, m), 8.19 (1H, s). | 85–86° C. |
| 19 | | 1.17 (3H, t, J = 7.5 Hz), 2.37 (3H, s), 2.55 (2H, q, J = 7.5 Hz), 3.26 (4H, t), 3.69 (4H, t), 3.98 (3H, s), 6.84 (1H, m), 6.91 (1H, s), 6.96 2h, m), 7.29 (1H, m), 8.19 (1H, s). | oil phase |
| 20 | | 1.18 (3H, t, J = 7.5 Hz), 2.39 (3H, s), 2.56 (2H, q, J = 7.0 Hz), 3.28 (4H, t, J = 4.5 Hz), 3.65 (4H, t, J = 4.5 Hz), 3.99 (3H, s), 6.90 (1H, s), 7.26 (2H, m), 8.23 (1H, s). | 162–163° C. |
| 21 | | 1.17 (3H, t, J = 7.5 Hz), 2.37 (3H, s), 2.55 (2H, q, J = 7.5 Hz), 3.27 (4H, t), 3.69 (4H, t), 3.98 (3H, s), 6.84 (1H, s), 6.98 (3H, m), 7.39 (1H, m), 8.35 (1H, s). | 94–94° C. |
| 22 | | 1.17 (3H, t, J = 7.5 Hz), 2.37 (3H, s), 2.56 (2H, q, J = 7.5 Hz), 3.27 (4H, t), 3.74 (4H, t), 3.98 (3H, s), 6.91 (1H, s), 6.98 (3H, m), 7.46 (1H, m), 8.19 (1H, s). | 99–101° C. |
| 23 | | 1.17 (3H, t, J = 7.5 Hz), 2.37 (3H, s), 2.55 (2H, q, J = 7.5 Hz), 3.25 (4H, t, J = 5.0 Hz), 3.67 (4H, t, J = 5.0 Hz), 3.98 (3H, s), 6.94 (2H, m), 7.29 (2H, m), 8.21 (1H, s). | 97–98° C. |
| 24 | | 1.17 (3H, t, J = 7.5 Hz), 2.38 (3H, s), 2.55 (2H, q, J = 7.5 Hz), 3.48 (4H, t, J = 5.0 Hz), 3.75 (4H, t, J = 5.0 Hz), 3.96 (3H, s), 6.84 (2H, m), 7.22 (1H, s), 8.18 (1H, s). | oil phase |
| 25 | | 1.17 (3H, t, J = 7.5 Hz), 2.38 (3H, s), 2.55 (2H, q, J = 7.5 Hz), 3.48 (4H, t, J = 5.0 Hz), | oil phase |

-continued

| example number | elementary analysis | $^1$H NMR (500 MHz, CDCl$_3$) δ | melting point |
|---|---|---|---|
| | | 3.75 (4H, t, J = 4.5 Hz), 3.96 (3H, s), 6.81 (1H, s), 6.84 (2H, m), 7.22 (1H, s), 8.18 (1H, s). | |
| 26 | | 1.18 (3H, t, J = 7.5 Hz), 2.34 (3H, s), 2.37 (3H, s), 2.57 (2H, q, J = 7.5 Hz), 2.96 (4H, t, J = 5.0 Hz), 3.65 (4H, t, J = 4.5 Hz), 3.97 (3H, s), 6.92 (1H, s), 7.02 (2H, m), 7.17 (2H, m), 8.21 (1H, s). | 129–130° C. |
| 27 | | 1.17 (3H, t, J = 7.5 Hz), 2.28 (3H, s), 2.37 (3H, s), 2.55 (2H, q, J = 7.5 Hz), 3.18 (4H, t, J = 5.0 Hz), 3.66 (4H, t, J = 5.0 Hz), 3.97 (3H,s), 6.87(2H,w), 6.91(1H,s), (2H, m), 8.19 (1H, s). | oil phase 7.11 |
| 28 | C$_{22}$H$_{30}$N$_4$O$_2$: theoretical, C, 69.08, H, 7.91, N, 14.65 experimental C, 68.48, H, 8.04, N, 14.04 | 1.18 (3H, t, J = 7.5 Hz), 2.25 (3H, s), 2.28 (3H, s), 2.37 (3H, s), 2.56 (2H, q, J = 7.5 Hz), 2.95 (4H, t), 3.65 (4H, t), 3.97 (3H, s), 6.89 (2H, m), 7.07 (1H, m), 8.21 (1H, s). | 99–100° C. |
| 29 | C$_{22}$H$_{30}$N$_4$O$_2$: theoretical C, 69.08, H, 7.91, N, 14.65 experimental C, 69.31, H, 7.82, N, 14.14 | 1.17 (3H, t, J = 7.5 Hz), 2.29 (6H, s), 2.44 (3H, s), 2.55(2H, q), 3.22 (4H, t, J = 4.5 Hz), 3.73 (4H, t, J = 4.5 Hz), 3.98 (3H, s), 6.42 (3H, s), 6.90 (1H, s), 8.35 (1H, s). | 83–84° C. |
| 30 | | 1.18 (3H, t, J = 8.0 Hz), 2.33 (6H, s), 2.39 (3H, s), 2.53 (2H, q, J = 7.5 Hz), 3.15 (4H, t, J = 5.0 Hz), 3.60 (4H, t, J = 5.0 Hz), 4.00 (3H, s), 6.91 (1H, s), 6.99 (3H, m), 8.24 (1H, s). | 122–123° C. |
| 31 | | 1.17 (3H, t, J = 7.5 Hz), 1.22 (3H, s), 1.23 (3H, s), 2.37 (3H, s), 2.55 (2H, q, J = 7.5 Hz), 2.87 (1H, m), 3.21 (4H, t), 3.67 (4H, t), 3.97 (3H, s), 6.90 (3H, m), 7.17 (2H, d), 8.35 (1H, s). | 99–100° C. |
| 32 | | 1.15 (3H, t, J = 7.5 Hz), 1.22 (3H, s), 1.23 (3H, s), 2.38 (3H, s), 2.94 (4H, t), 3.07 (1H, m), 3.16 (4H, t), 4.00 (3H, s), 6.84 (1H, s), 7.16 (3H, m), 7.30 (1H, m), 8.22 (1H, s). | 137–139° C. |
| 33 | | 0.91 (3H, t, J = 7.5 Hz), 1.17 (3H, t, J = 7.5 Hz) 1.35 (2H, m), 1.59 (2H, m), 2.37 (3H, s), 2.55 (4H, q, J = 4.0 Hz), 3.20 (4H, t, J = 5.0 Hz), 3.66 (4H, t, J = 5.0 Hz), 3.97 (3H, s); 6.82 (2H, m), 6.88 (1H, s), 7.11 (2H, m), 8.19 (1H, s). | 72–73° C. |
| 34 | | 1.17 (3H, t, J = 7.5 Hz), 2.37 (3H, s), 2.56( 3H, s), 2.57 (2H, q, J = 7.5 Hz), 3.55 (4H, t), 3.69 (4H, t), 3.98 (3H, s), 6.88 (3H, m), 7.91 (2H, m), 8.18 (1H, s). | 149–150° C. |
| 35 | | 1.15 (3H, t, J = 7.5 Hz), 2.37 (3H, s), 2.54 (2H, q, J = 7.5 Hz), 2.89 (4H, t, J = 4.8 Hz), 3.38 (4H, t, J = 4.8 Hz), 3.95 (3H, s), 6.78 (1H, s), 7.03 (1H, d), 7.12 (1H, m), 7.31 (3H, m), 7.41 (2H, m), 7.63 (2H, m), 8.17 (1H, s). | oil phase |
| 36 | | 1.18 (3H, t, J = 7.5 Hz), 2.38 (3H, s), 2.56 (2H, q, J = 7.5 Hz), 3.32 (4H, t), 3.72 (4H, t), 3.99 (3H, s), 6.92 (1H, s), 7.04 (2H, m), 7.40 (2H, m), 7.57 (5H, m), 8.20 (1H, s). | 160–161° C. |
| 37 | | 1.18 (3H, t, J = 7.5 Hz), 2.38 (3H, s), 2.97 (4H, t), 3.70 (4H, t), 3.98 (1H, s), 6.92 (2H, m), 7.11 (2H, m), 8.19 (1H, s). | oil phase |
| 38 | C$_{20}$H$_{26}$N$_4$O$_3$: theoretical, C, 64.85, H, 7.07, N, 15.12 experimental, C, 59.89, H, 7.17, N, 14.73 | 1.16 (3H, t, J = 7.5 Hz), 2.39 (3H, s), 3.23 (4H, t, J = 5.0 Hz), 3.67 (4H, t), 3.98 (3H, s), 6.39 (1H, d), 6.45 (1H, s), 6.51 (1H, d), 6.90 (1H, s), 7.13 (1H, m), 8.17 (1H, s). | 148–149° C. |
| 39 | | 1.18 (3H, t, J = 7.5 Hz), 2.37 (3H, s), 2.55 (2H, q, J = 7.5 Hz), 3.16 (4H, t), 3.73 (4H, t), 3.98 (3H, s), 6.80 (2H, m), 6.91 (2H, m), 8.17 (1H, s) | 103–104° C. |
| 40 | | 1.17 (3H, t, J = 7.5 Hz), 2.29 (3H, s), 2.38 (3H, s), 2.56 (2H, q, J = 7.5 Hz), 3.24 (4H, t), 3.72 (4H, t), 3.99 (3H, s), 6.90 (1H, s), 7.03 (4H, m), 8.21 (1H, s). | 161–162° C. |
| 41 | C$_{22}$H$_{28}$N$_4$O$_4$: theoretical, C, 64.06, H, 6.84, N, 13, 58 | 1.17 (3H, t, J = 7.5 Hz), 2.29 (3H, s), 2.38 (3H, t), 2.56 (2H, q, J = 7.5 Hz), 3.28 (4H, t, | 90°91° C. |

| example number | elementary analysis | ¹H NMR (500 MHz, CDCl$_3$) δ | melting point |
|---|---|---|---|
| | experimental<br>C, 64.31, H, 13.50, N, 7.00 | J = 5.0 Hz), 3.68 (4H, t), 3.99 (3H, s), 6.65 (2H, m), 6.84 (1H, d), 6.89 (1H, s), 7.30 (1H, m), 8.19 (1H, s). | |
| 42 | | 1.17 (3H, t, J = 7.5 Hz), 2.37 (3H, s), 2.55 (2H, q, J = 7.5 Hz), 3.18 (4H, t), 3.68 (4H, t), 3.99 (3H, s), 6.89 (2H, m), 6.99 (2H, m), 8.19 (1H, s). | oil phase |
| 43 | | 1.18 (3H, t, J = 7.5 Hz), 2. 37 (3H, s), 2.54 (2H, q, J = 7.5 Hz), 2.89 (3H, s), 2.97 (4H, t), 3.65 (4H, t), 3.96 (3H, s), 6.77 (2H, m), 6.94 (1H, s), 7.03 (1H, d), 7.13 (1H, m). | 108–109° C. |
| 44 | | 1.17 (3H, t, J = 7.5 Hz), 2.26 (3H, s), 2.57 (2H, q), 3.17 (4H, t), 3.79 (1H, d), 4.00 (3H, s), 6.91 (1H, s), 7.09 (1H, d), 7.42 (1H, m), 7.50 (3H, m), 7.59 (1H, d), 7.84 (1H, d). | 159–160° C. |
| 45 | | 1.17 (3H, t, J = 7.5 Hz), 2.47 (3H, s), 2.56 (2H, q), 3.04 (4H, t), 4.05 (3H, s), 6.97 (1H, s), 7.49 (4H, m), 8.01 (2H, m), 8.27 (2H, m), 8.43 (1H, s). | oil phase |
| 46 | | 1.18 (3H, t, J = 7.5 Hz), 2.26 (3H, s), 2.39 (3H, s), 2.56 (2H, q, J = 7.5 Hz), 2.82 (2H, m) 3.20 (2H, m), 3.46 (2H, m), 3.78 (3H, s), 3.99 (2H, m), 4.14 (3H, s), 6.71 (1H, d), 6.82 (1H, d), 6.91 (1H, s), 7.04 (1H, m), 8.25 (1H, s). | 151–152° C. |
| 47 | C$_{22}$H$_{30}$N$_4$O$_3$: theoretical,<br>C, 66.31, H, 7.59, N, 14.06<br>experimental<br>C, 66.46, H, 7.75, N, 13.71 | 1.17 (3H, t, J = 7.5 Hz), 2.37 (3H, s), 2.49 (3H, s), 2.55 (2H, q, J = 7.5 Hz), 3.11 (4H, t), 3.77 (4H, t), 3.86 (3H, s), 3.96 (3H, s), 6.77 (3H, m), 8.37 (1H, s). | 90–91° C. |
| 48 | C$_{22}$H$_{30}$N$_4$O$_3$:<br>C, 66.31, H, 7.59, N, 14.06<br>experimental<br>C, 65.24, H, 7.49, N, 13.91 | 1.17 (3H, t, J = 7.5 Hz), 2.23 (3H, s), 2.37 (3H, s), 2.38 (3H, s), 2.53 (2H, q, J = 7.5 Hz), 2.95 (4H, t, J = 4.8 Hz), 3.65 (4H, t, J = 4.6 Hz), 3.96 (3H, s), 3.98 (3H, s), 6.57 (2H, m), 6.84 (1H, s), 7.03 (1H, s), 8.20 (1H, s). | 84–85° C. |
| 49 | | 1.17 (3H, t, J = 7.5 Hz), 2.37 (3H, s), 2.55 (2H, q, J = 7.5 Hz), 3.12 (4H, t), 3.70 (4H, t), 3.89 (3H, s), 3.97 (3H, s), 6.80 (2H m), 6.94 (1H, s), 8.21 (1H, s). | 97–98° C. |
| 50 | | 1.17 (3H, t, J = 7.5 Hz), 2.37 (3H, s), 2.57 (2H, q, J = 7.5 Hz), 3.27 (4H, t), 3.69 (4H, t), 3.80 (3H, s), 3.98 (3H,s), 6.50 (1H, m), 6.90 (1H, s), 7.54 (1H, m), 7.71 (1H, m), 8.19 (1H, s). | oil phase |
| 51 | | 1.19 (3H, t, J = 7.5 Hz), 2.37 (3H, s), 2.55 (2H, q, J = 7.5 Hz), 3.13 (4H, t), 3.67 (4H, t), 3.78 (3H, s), 3.97 (3H, s), 6.87 (3H, m), 8.19 (1H, s). | 94–95° C. |
| 52 | | 1.17 (3H, t, J = 7.5 Hz), 2.37 (3H, s), 2.55 (2H, q, J = 7.5 Hz), 3.15 (4H, t), 3.69 (4H, t), 3.83 (3H, s), 3.98 (3H, s), 6.46 (1H, d), 6.69 (1H, d), 6.90 (1H, s), 8.18 (1H, s). | 149–150° C. |
| 53 | | 1.17 (3H, t, J = 7.5 Hz), 2.31 (3H, s), 2.37 (3H, s), 2.55 (2H, q, J = 7.5 Hz), 3.14 (4H, t), 3.66 (4H, t), 3.79 (3H, s), 3.95 (3H, s), 6.77 (1H, s), 6.92 (2H, m), 8.18 (1H, m), 7.53 (2H, m), 8.21 (1H, s). | 128–135° C. |
| 54 | | 1.17 (3H, t, J = 7.5 Hz), 2.37 (3H, s), 2.56 (2H, q, J = 7.5 Hz), 3.19 (4H, t), 3.73 (4H, t), 3.93 (3H, s), 3.98 (3H, s), 6.82 (1H, s), 6.84 (2H, m), 7.31 (2H, m), 7.42 (2H, m), 7.53 (2H, m), 8.21 (1H, s). | 134–135° C. |
| 55 | C$_{22}$H$_{27}$N$_4$O$_3$Cl$_1$:theoretical<br>C, 60.20, H, 6.50, N, 13.37<br>experimental,<br>C, 59.33, H, 6.16, N, 12.80 | 1.17 (3H, t, J = 7.5 Hz), 2.23 (3H, s), 2.38 (3H, s), 2.56 (2H, q, J = 7.5 Hz), 2.95 (4H, t, J = 5.0Hz), 3.66 (4H, t), 3.99 (3H, s), 6.85 (1H, d), 6.64 (1H, d), 6.91 (1H, s), 7.05 (1H, m), 8.21 (1H, s). | 188–189° C. |
| 56 | C$_{21}$H$_{28}$N$_4$O$_3$: theoretical,<br>C, 65.60, H, 7.34, N, 14.57<br>experimental<br>C, 65.65, H, 7.32, N, 14.40 | 1.18 (3H, t, J = 8.0 Hz), 2.36 (3H, s), 2.41 (3H, s), 2.57 (2H, q, J = 7.5 Hz), 2.93 (2H, m), 3.20 (2H, m), 3.43 (2H, m), 3.99 (3H, s), 4.11 (2H, m), 6.60 (1H, d), 6.83 (2H, s). | 208–211° C. |
| 57 | | 1.18 (3H, t, J = 7.5 Hz), 2.29 (3H, s), 2.38 (3H, s), 2.56 (2H, q, J = 7.5 Hz), 2.97 (4H, t), 3.71 (4H, t), 3.98 (3H, s), 6.69 (1H, d), 6.82 (1H, s), 6.90 (1H, s), 7.05 (1H, | 192–193° C. |

-continued

| example number | elementary analysis | $^1$H NMR (500 MHz, CDCl$_3$) δ | melting point |
|---|---|---|---|
| | | d), 8.18 (1H, s). | |
| 58 | | 1.13 (3H, t, J = 7.5 Hz), 2.24 (3H, s), 2.55 (2H, q, J = 7.5 Hz), 3.48 (4H, t, J = 5.0 Hz), 3.75 (4H, t, J = 5.0 Hz), 3.97 (3H, s), 6.89 (2H, m), 7.20 (1H, s), 8.35 (1H, s). | 74–75° C. |
| 59 | | 1.17 (3H, t, J = 7.5 Hz), 2.37 (3H, s), 2.55 (2H, q, J = 7.5 Hz), 3.04 (4H, t, J = 5.0 Hz), 3.68 (4H, t, J = 5.0 Hz), 3.98 (3H, s), 6.94 (2H, m), 6.98 (1H, m), 8.19 (1H, s). | 85–86° C. 85–86° C. |
| 60 | C$_{22}$H$_{30}$N$_4$O$_3$: theoretical, C, 66.31, H, 7.59, N, 14.06 experimental, C, 65.38, H, 7.65, N, 13.74 | 1.11 (3H, t, J = 7.5 Hz), 2.38 (3H, s), 2.54 (2H, q, J = 7.5 Hz), 3.05 (4H, t, J = 5.0 Hz), 3.53 (4H, t, J = 4.5 Hz), 3.86 (3H, s), 3.95 (3H, s), 4.33 (2H, d), 6.86 (1H, d), 6.93 (2H, m), 7.01 (1H, m), 7.25 (1H, s). | oil phase |
| 61 | C$_{21}$H$_{27}$N$_4$O$_2$F$_1$: theoretical C, 65.27, H, 7.04, N, 14.50 experimental C, 65.87, H, 7.35, N, 14.48 | 1.14 (3H, t, J = 7.5 Hz), 2.40 (3H, s), 2.54 (2H, q, J = 7.5 Hz), 3.04 (4H, t, J = 5.0 Hz), 3.52 (4H, t, J = 5.0 Hz), 4.33 (2H, d), 6.92 (2H, m), 7.06 (2H, m), 7.32 (1H, s). | oil phase |
| 62 | | 1.16 (3H, t, J = 7.5 Hz), 2.40 (3H, s), 2.54 (2H, q, J = 7.5 Hz), 3.07 (4H, t, J = 5.0 Hz), 3.50 (4H, t, J = 5.0 Hz), 3.95 (3H, s), 4.34 (2H, d), 6.85 (2H, m), 6.97 (2H, m), 7.32 (1H, s). | oil phase |
| 63 | | 1.15 (3H, t, J = 8.0 Hz), 2.38 (3H, s), 2.54 (2H, q, J = 7.5 Hz), 3:16 (4H, t, J = 5.0 Hz), 3.49 (4H, t, J = 5.0 Hz), 3.96 (3H, s), 4.33 (2H, d), 6.75 (1H, m), 6.85 (2H, m), 7.15 (1H, m), 7.46 (2H, s). | oil phase |
| 64 | | 1.15 (3H, t, J = 7.5 Hz), 2.40 (3H, s), 2.53 (2H, q, J = 7.5 Hz), 2.76 (2H, t, J = 6.5Hz), 3.05 (4H, t, J = 4.8 Hz), 3.47 (6H, m), 3.93 (3H, s), 6.87 (2H, m), 6.97 (2H, m), 7.26 (1H, s). | oil phase |
| 65 | | 1.14 (3H, t, J = 7.5 Hz), 2.43 (3H, s), 2.51 (2H, q, J = 7.5 Hz), 2.76 (2H, m), 3.00 (4H, t, J = 5.0 Hz), 3.44 (2H, m), 3.50 (4H, t), 3.87 (3H, s), 3.93 (3H, s), 6.72 (1H, m), 6.92 (2H, m), 7.01 (1H, m), 7.16 (1H, s). | oil phase |
| 66 | | 1.16 (3H, t, J = 7.5 Hz), 1.80 (2H, q), 2.40 (3H, s), 2.53 (2H, q), 2.58 (2H, t), 3.26 (2H, q), 3.89 (3H, s), 3.93 (3H, s), 6.92 (4H, m), 7.16 (1H, s). | oil phase |
| 67 | | 1.15 (3H, t, J = 7.5 Hz); 1.38 (2H, m), 1.58 (4H, m), 2.39 (3H, s), 2.52 (4H, m), 3.06 (4H, t), 3.25 (2H, m), 3.55 (4H, t), 3.87 (3H, s), 3.91 (3H, s), 6.88 (2H, m), 6.94 (2H, m), 7.46 (1H, s). | 128–129° C. |
| 68 | | 1.15 (3H, t, J = 7.5 Hz), 1.33 (6H, m), 1.52 (2H, m), 2.39 (3H, s), 2.52 (4H, m), 3.05 (4H, t), 3.25 (2H, m), 3.54 (4H, t), 3.87 (3H, s), 3.90 (3H, s), 6.87 (2H, m), 6.93 (2H, m), 7.10 (1H, s). | 118–120° C. |
| 69 | | 1.20 (3H, t), 2.39 (3H, s), 2.58 (2H, q), 2.83 (4H, t), 3.20 (6H, brs), 3.90 (3H, s), 3.98 (3H, s), 7.00 (4H, m), 8.40 (1H,s). | 164 . 165° C. |
| 70 | | 1.18 (3H, t), 2.39 (3H, s), 2.56 (2H, q), 2.77 (4H, t), 3.21 (2H, m), 3.28 (4H,t), 6.82 (2H, m), 6.90 (1H, s), 7.19 (1H, m), 8.37 (1H, s). | 120–123° C. |
| 71 | | 1.18 (3H, t), 2.39 (3H, s), 2.56 (2H, q), 2.81 (4H, t), 3.20 (6H, brs), 3.97 (3H, s), 7.04 (4H, m), 8.38 (1H, s). | 139–140° C. |
| 72 | | 1.16 (3H, t, J = 7.5 Hz), 2.36 (3H, s), 2.54 (6H, m), 3.96 (3H, s), 6.85 (1H, s), 7.33 (5H, s). | 96–97° C. |
| 73 | | 1.16 (3H, t, J = 7.5 Hz), 2.36 (3H, s), 2.52 (6H, m), 3.53 (6H, m), 3.81 (3H, s), 3.95 (3H, s), 6.84 (1H, s), 6.88 (2H, m), 7.27 (2H, m), 8.16 (1H, s). | 96–98° C. |
| 74 | | 1.17 (3H, t, J = 7.5 Hz), 2.37 (3H, s), 2.52 (2H, q), 2.65 (4H, t), 3.61(6H, m), 3.83 (3H, s), 3.95 (3H, s), 6.83 (1H, s), 6.90 (2H, m), 6.97 (2H, m), 8.15 (1H, s). | 83–84° C. |
| 75 | | 1.16 (3H, t, J = 7.5 Hz), 2.37 (3H, s), 2.54 (6H, m), 3.53 (6H, m), 3.97 (3H, s), 6.85 (1H, s), 7.02 (2H, m), 7.32 (2H, m), | 74–75° C. |

-continued

| example number | elementary analysis | $^1$H NMR (500 MHz, CDCl$_3$) δ | melting point |
|---|---|---|---|
| | | 8.17 (1H, s). | |
| 76 | | 1.17 (3H, t, J = 7.5 Hz), 1.39 (3H, t, J = 7.0 Hz), 2.35 (3H, s), 2.55 (2H, q, J = 5.0 Hz), 3.13 (4H, t, J = 4.6 Hz), 3.68 (4H, t, J = 4.6 Hz), 3.89 (3H, s), 4.42 (2H, q, J = 9.3 Hz), 6.90 (1H, d), 6.96 (2H, m), 7.04 (1H, m), 8.21 (1H, s). | 114–115° C. |
| 77 | | 1.17 (3H, t, J = 7.5 Hz), 1.40 (3H, t, J = 7.0 Hz), 2.38 (3H, s), 2.55 (2H, q, J = 7.5 Hz), 3.14 (4H, t, J = 4.5 Hz), 3.68 (4H, t, J = 4.5 Hz), 4.43 (2H, q, J = 7.0 Hz), 6.96 (2H, m), 7.08 (2H, m), 8.19 (1H, s). | 126–127° C. |
| 78 | | 1.17 (3H, t, J = 7.5 Hz), 1.40 (3H, t, J = 7.5 Hz), 2.35 (3H, s), 2.55 (2H, q, J = 7.5 Hz), 3.27 (4H, t, J = 5.0 Hz), 3.66 (4H, t, J = 5.0 Hz), 4.43 (2H, q, J = 7.0 Hz), 6.79 (1H, d), 6.81 (1H, d), 6.86 (1H, s), 6.94 (1H, s), 7.19 (1H, m), 8.18 (1H, s). | 101–102° C. |
| 79 | | 1.17 (3H, t, J = 7.5 Hz), 1.40 (3H, t, J = 7.0 Hz), 1.49 (3H, t, J = 6.9 Hz), 2.35 (3H, s), 2.55 (2H, q), 3.14 (4H, t), 3.68 (4H, t), 4.10 (2H, q), 4.44 (2H, q), 6.87 (1H, d), 6.92 (2H, m), 6.96 (1H, s), 7.00 (1H, m), 8.20 (1H, s). | oil phase |
| 80 | | 1.22 (3H, t, J = 7.5 Hz), 2.31 (3H, s), 2.58 (2H, q, J = 7.5 Hz), 3.08 (4H, t), 3.66 (4H, t), 3.88 (3H, s), 6.96 (3H, m), 7.13 (2H, m), 7.23 (2H, m), 7.36 (2H, m), 8.36 (1H, s). | 104–105° C. |
| 81 | | 1.22 (3H, t, J = 7.5 Hz), 2.31 (3H, s), 2.60 (2H, q, J = 7.5 Hz), 3.22 (4H, t), 3.66 (4H, t), 3.88 (3H, s), 6.93 (1H, s), 6.96 (3H, m), 7.13 (2H, m), 7.23 (2H, m), 7.36 (2H, m), 8.36 (1H, s). | 120–121° C. |
| 82 | | 1.22 (3H, t, J = 7.5 Hz), 2.29 (3H, s), 2.34 (3H, s), 2.60 (2H, q, J = 7.5 Hz), 3.24 (4H, t, J = 5.0 Hz), 3.63 (4H, t, J = 4.5 Hz), 6.62 (2H, m), 6.80 (1H, d), 6.93 (1H, s), 7.10 (2H, m), 7.17 (1H, m), 7.27 (1H, m), 7.46 (2H, m), 8.34 (1H, s). | 52–53° C. |
| 83 | | 1.22 (3H, t, J = 7.5 Hz), 2.31 (3H, s), 2.60 (2H, q), 3.11 (4H, t, J = 4.8 Hz), 3.65 (4H, t, J = 4.8 Hz), 6.99 (3H, m), 7.09 (4H, m), 7.36 (2H, m)m 8.35 (1H, s). | 166–167– C. |
| 84 | | 1.23 (3H, t, J = 7.5 Hz), 2.28 (3H, s), 2.31 (3H, s), 2.60 (2H, q, J = 7.5 Hz), 3.19 (4H, t, J = 5.0 Hz), 3.95 (4H, t), 6.55 (3H, m), 6.94 (1H, s), 7.09 (2H, m), 7.20 (1H, m), 7.38 (2H, m), 8.35 (1H, s). | oil phase |
| 85 | | 1.25 (3H, t, J = 7.2 Hz), 2.30 (3H, s), 2.60 (2H, q, J = 7.5 Hz), 3.21 (4H, t, J = 5.2 Hz), 3.62 (4H, t), 3.77 (6H, s), 6.08 (3H, m), 7.13 (2H, m), 6.93 (1H, s), 7.16 (1H, m), 7.36 (2H, m), 8.34 (1H, s). | 94–95° C. |
| 86 | | 1.19 (3H, t, J = 7.5 Hz), 2.37 (3H, s), 2.55 (2H, q, J = 7.5 Hz), 3.26 (4H, t, J = 5.0 Hz), 3.78 (4H, t, J = 6.0 Hz), 3.98 (3H, s), 6.91 (1H, s), 6.97 (2H, m), 7.31 (1H, m), 8.91 (1H, s). | 156–157° C. |
| 87 | | 1.22 (3H, t, J = 8.0 Hz), 2.31 (3H, s), 2.60 (2H, q, J = 7.5 Hz), 3.10 (4H, t), 3.66 (4H, t), 3.99 (3H, s), 6.79 (1H, m), 6.91 (1H, s), 6.93 (2H, m), 7.10 (2H, m), 7.16 (1H, m), 7.38 (2H, m), 8.34 (1H, s). | 117–118° C. |
| 88 | | 1.23 (3H, t, J = 7.5 Hz), 2.18 (3H, s), 2.60 (2H, q, J = 7.5 Hz), 3.22 (4H, t, J = 4.5 Hz), 3.95 (4H, t), 6.40 (1H, m), 6.52 (2H, m), 7.13 (2H, m), 7.37 (2H, m), 8.32 (1H, s). | 92–93° C. |
| 89 | | 1.24 (3H, t, J = 7.5 Hz), 2.52 (3H, s), 2.66 (2H, q, J = 8.0 Hz), 3.21 (4H, t), 3.45 (3H, s), 3.82 (4H, t), 4.12 (3H, s), 7.02 (4H, m), 7.43 (1H, s). | 185–186° C. |
| 90 | | 1.25 (3H, t, J = 7.5 Hz), 2.52 (3H, s), 2.65 (2H, q), 3.45 (3H, s), 3.89 (6H, s), 6.95 (3H, m), 7.43 (1H, s). | 1-2–103° C. |
| 91 | | 1.22 (3H, t, J = 7.5 Hz), 2.53 (3H, s), 2.66 (2H, q, J = 7.5 Hz), 3.35 (4H, t), 3.47 (3H, | oil phase |

-continued

| example number | elementary analysis | ¹H NMR (500 MHz, CDCl₃) δ | melting point |
|---|---|---|---|
| | | s), 3.81 (4H, t), 4.23 (1H, q, J = 5.7 Hz), 6.88 (2H, m), 6.94 (1H, s), 7.22 (2H, m), 7.71 (1H, s). | |
| 92 | | 1.22 (3H, t, J = 7.5 Hz), 2.49 (3H, s), 2.63 (2H, q, J = 8.0 Hz), 3.11 (4H, t, J = 5.0 Hz) 3.70 (4H, t, J = 5.0 Hz), 3.72 (6H, s), 6.68 (1 H, m), 6.88 (2H, m), 7.05 (1H, m), 7.88 (1 H, s), 8.23 (1H, s). | 161–162° C. |
| 93 | | 1.21 (3H, t, J = 7.5 HZ), 2.42 (3H, s), 2.63 (2H, q, J = 7.5 Hz), 3.24 (4H, t, J = 5.0 Hz), 3.67 (4H, t, J = 5.0 Hz), 3.78 (6H, s), 6.05 (1H, s), 6.09 (2H, s), 7.89 (1H, s), 8.26 (1H, s). | 179–180° C. |
| 94 | | 1.20 (3H, t, J = 7.5 Hz), 2.40 (3H, s), 2.57 (2H, q, J = 7.5 Hz), 3.02 (4H, t), 3.09 (4H, t), 3.28 (4H, t), 3.68 (4H, t), 6.80 (2H, d), 6.82 (1H, d), 6.90 (1H, s), 7.22 (1H, m), 8.22 (1H, s). | oil phase |
| 95 | | 1.20 (3H, t, J = 7.5 Hz), 1.48 (9H, s), 2.39 (3H, s), 2.58 (2H, q), 2.95 (4H, t), 3.28 (4H, t), 3.57 (4H, t), 3.67 (4H, t), 6.79 (1H, dd), 6.87 (1H, dd), 7.21 (1H, m), 7.26 (1H, s), 8.24 (1H, s). | 188–189° C. |
| 96 | | 1.20 (3H, t, J = 7.5 Hz), 1.48 (9H, s), 2.39 (3H, s), 2.58 (2H, q), 2.95 (4H, t), 3.12 (4H, t), 3.57 (4H, t), 3.70 (4H, t), 3.91 (3H, s), 6.94 (3H, m), 7.06 (1H, m), 7.58 (1H, s), 8.25 (1H, s). | 152–153° C. |
| 97 | $C_{21}H_{28}N_4O_2S_1$: theoretical, C, 62.97, H, 7.05, N, 13.99, S, 8.00, experimental, C, 62.61, H, 6.96, N, 14.08, S, 7.77, | 1.19 (3H, t, J = 7.5 Hz), 2.39 (3H, s), 2.57 (2H, q, J = 7.5 Hz), 3.16 (4H, t, J = 5.0 Hz), 3.89 (3H, s), 3.96 (3H, s), 4.10 (4H, t, J = 4.5 Hz), 6.89 (1H, m), 6.93 (2H, m), 7.04 (1H, m), 8.11 (1H, s). | 133–134° C. |
| 98 | | 1.17 (3H, t), 2.47 (3H, s), 2.55 (2H, q, J = 7.5 Hz), 3.39 (4H, t, J = 5.1 Hz), 3.98 (3H, s), 4.18 (4H, t), 6.79 (1H, m), 6.90 (2H, m), 7.19 (1H, m), 8.11 (1H, s). | 90–91° C. |
| 99 | | 1.19 (3H, t, J = 7.5 Hz), 2.39 (3H, s), 2.58 (2H, q, J = 7.5 Hz), 3.19 (4H, t, J = 5.0 Hz), 3.96 (3H, s), 4.09 (4H, t, J = 5.0 Hz), 6.95 (2H, m), 7.00 (2H, m), 8.11 (1H, s). | 132–133° C. |
| 100 | $C_{22}H_{30}N_4O_3S_1$: theoretical, C, 61.37, H, 7.02, N, 13.01, S, 7.45, experimental C, 61.47, H, 7.25, N, 13.21, S, 7.47, | 1.19 (3H, t, J = 7.5 Hz), 2.40 (3H, s), 2.58 (2H, q, J = 7.5 Hz), 3.36 (4H, t, J = 4.5 Hz), 3.75 (6H, s), 3.96 (3H, s), 4.13 (4H, t), 6.09 (3H, m), 8.13 (1H, s). | 166–167° C. |
| 101 | | 1.20 (3H, t, J = 7.5 Hz), 2.40 (3H, s), 2.58 (2H, q, J = 8.0 Hz), 3.37 (4H, t), 3.96 (3H, s), 4.15 (4H, t), 6.98 (2H, m), 7.46 (1H, s), 8.13 (1H, s). | 166–167° C. |
| 102 | | 1.18 (3H, t, J = 8.0 Hz), 2.40 (3H, s), 2.55 (2H, q, J = 7.5 Hz), 3.11 (4H, t), 3.75 (2H, t), 3.87 (2H, t), 3.89 (3H, s), 3.97 (3H, s), 6.86 (1H, d), 6.94 (2H, m), 7.04 (1H, m), 7.26 (1H, s). | 89–90° C. |
| 103 | | 1.26 (3H, t, J = 7.5 Hz), 2.40 (3H, s), 2.55 (2H, q), 3.25 (4H, t), 3.72 (2H, t), 3.84 (2H, t), 3.93 (3H, s), 6.82 (1H, d), 6.86 (1H, d), 6.92 (1H, s), 7.04 (1H, s), 7.22 (1H, m), 7.46 (1H, s). | 119–120° C. |
| 104 | | 1.17 (3H, t, J = 7.5 Hz), 2.39 (3H, s), 2.53 (2H, q, J = 7.5 Hz), 3.23 (4H, t, J = 5.0 Hz), 3.64 (2H, t), 3.79 (6H, s), 3.79 (2H, t), 5.96 (1RH, s), 6.12 (2H, s), 7.30 (1H, s). | oil phase |
| 105 | | 1.17 (3H, t, J = 7.5 Hz), 2.42 (3H, s), 2.56 (2H, q, J = 7.5 Hz), 3.01(4H, t), 3.78 (4H, t), 3.87 (3H, s), 3.93 (3H, s), 5.11 (2H, s), 6.91 (3H, s), 7.03 (1H, m), 7.33 (1H, s). | oil phase |
| 106 | | 1.15 (3H, t, J = 7.5 Hz), 2.42 (3H, s), 2.54 (2H, q), 3.15 (4H, t), 3.64 (4H, t), 3.93 (3H, s), 3.96 (3H, s), 4.59 (2H, s), 6.85 (3H, m), 7.15 (1H, s), 7.33(1H, s). | oil phase |
| 107 | | 2.19 (3H, s), 2.34 (3H, s), 3.26( 4H, t), 3.69 (4H, t), 3.97 (3H, s), 6.82 (1H, s), 6.94 (3H, m), 7.30 (2H, m), 8.14 (1H, s). | 140"141° C. |
| 108 | $C_{20}H_{26}N_4O_3$: theoretical, C, 64.85, H, 7.07, N, 15.12 | 1.55 (3H, s), 2.19 (3H, s), 2.33 (3H, s), 3.12 (4H, t), 3.69 (4H, t), 3.89(3H, s), | 135–136° C. |

-continued

| example number | elementary analysis | $^1$H NMR (500 MHz, CDCl$_3$) δ | melting point |
|---|---|---|---|
|  | experimental, C, 65.13, H, 7.24, N, 15.10 | 3.97 (3H, s), 6.89 (2H, m), 6.90 (1H, s), 7.04 (2H, m), 8.16 (1H, s). |  |
| 109 | C$_{19}$H$_{23}$N$_4$O$_2$Cl$_1$: theoretical, C, 60.88, H, 6.18, N, 14.95 experimental, C, 60.87, H, 6.28, N, 14.86 | 2.19 (3H, s), 2.34 (3H, s), 3.27 (4H, t, J = 5.2 Hz), 3.66 (4H, t, J = 5.0 Hz), 3.98 (3H, s), 6.80 (1H, d), 6.86 (2H, m), 6.90 (1H, s), 7.21 (1H, m), 8.14 (1H, s). | 95–96° C. |
| 110 |  | 2.19 (3H, s), 2.34 (3H, s), 3.14 (4H, t, J = 4.9 Hz), 3.68 (4H, t, J = 4.8 Hz), 3.98 (3H, s), 6.88 (1H, s), 6.98(2H, m), 7.09 (2H, m), 8.15 (1H, s). | 164–167° C. |
| 111 |  | 2.20 (3H, s), 2.39 (3H, s), 3.29 (4H, t, J = 5.0 Hz), 3.67 (4H, t, J = 5.0 Hz), 4.04 (3H, s), 6.30 (1H, m), 6.38(2H, d), 6.86 (1H, s), 8.18 (1H, s). | 133–134° C. |
| 112 |  | 2.19( 3H, s), 2.35 (3H, s), 2.99 (4H, t), 3.72 (4H, t), 3.98 (3H, s), 6.90 (2H, m), 7.15 (2H, m), 8.14 (1H, s). | 174–175° C. |
| 113 |  | 2.18 (3H, s), 2.33 (3H, s), 3.25 (4H, t, J = 5.0 Hz), 3.67 (4H, t, J = 4.3 Hz), 3.97 (3H, s), 6.38 (1H, d), 6.46 (1H, s), 6.54 (1H, d), 6.87 (1H, s), 7.13 (1H, t), 8.13 (1H, s). | 176–178° C. |
| 114 |  | 2.18 (3H, s), 2.33 (3H, s), 3.12 (4H, t), 3.68 (4H, t), 3.97 (3H, s), 6.80 (2H, m), 6.91 (2H, m), 8.13 (1H, s) | 168–169° C. |
| 115 |  | 2.09 (3H, s), 2.29 (3H, s), 2.34 (3H, s), 3.27 (4H, t, J = 5.0 Hz), 3.67 (4H, t, J = 5.0 Hz), 3.98 (3H, s), 6.44 (2H, m), 6.81 (1H, m), 6.88 (1H, s), 8.14 (1H,s). | 108–109° C. |
| 116 |  | 2.19 (3H, s), 2.28 (3H, s), 2.34 (3H, s), 3.22 (4H, t), 3.68 (4H, t), 3.98 (3H, s), 6.87 (1H, s), 7.01 (4H, m), 8.14 (1H, s). | 159–160° C. |
| 117 |  | 2.04 (3H, s), 2.31 (3H, s), 2.34 (3H, s), 3.20 (4H, t), 3.76 (4H, t), 3.81 (3H, s), 3.98 (3H, s), 6.86 (1H, s), 7.01 (3H, m), 8.15 (1H, s). | 139–140° C. |
| 118 | C$_{21}$H$_{28}$N$_4$O$_4$: theoretical, C, 62.98, H, 7.05, N, 13.99 experimental, C, 63.21, H, 7.19, N, 13.96 | 2.18 (3H, s), 2.33 (3H, s), 3.25 (4H, t, J = 5.0 Hz), 3.67 (4H, t), 3.80 (6H, s), 3.97 (3H, s), 6.07 (3H, m), 6.86 (1H, s), 8.14 (1H, s). | 150–151° C. |
| 119 | C$_{21}$H$_{30}$N$_4$O$_2$: C, 68.45, H, 7.66, N, 15.20 experimental C, 68.26, H, 7.97, N, 14.99 | 2.19 (3H, s), 2.26 (3H, s), 2.28 (3H, s), 2.34 (3H, s), 2.94 (4H, t), 3.66 (4H, t), 3.97 (3H, s), 6.89 (3H, m), 8.33 (1H, s). | 134–135° C. |
| 120 |  | 2.16 (3H, s), 2.29 (6H, s), 2.33 (3H, s), 3.23 (4H, t), 3..66 (4H, t), 3.97 (3H, s), 6.53 (3H, m), 6.87 (1H, s), 8.14 (1H, s). | 125–126° C. |
| 121 |  | 2.19 (3H, s), 2.26 (3H, s), 2.34 (3H, s), 2.95 (4H, t, J = 4.8 Hz), 3.64 (4H, t, J = 4.8 Hz), 3.78 (3H, s), 3.97 (3H, s), 6.57 (1H, d), 6.58 (1H, s), 7.11 (1H, d), 8.32 (1H, s). | 127–130° C. |
| 122 |  | 2.19 (3H, s), 2.30 (3H, s), 2.42 (3H, s), 2.94 (4H, t), 3.69 (4H, t), 3.97 (3H, s), 6.69 (1H, d), 6.82 (1H, s), 6.88 (1H, s), 7.04 (1H, d), 8.14 (1H, s). | 184–185° C. |
| 123 |  | 2.04 (3H, s), 2.33 (3H, s), 3.15 (4H, t), 3.67 (4H, t), 3.89 (3H, s), 3.97 (3H, s), 6.65 (1H, d), 6.81 (1H, d), 8.14 (1H, s). | 172–176° C. |
| 124 |  | 2.20 (3H, s), 2.48 (3H, s), 3.17 (4H, t), 3.76 (4H, t), 4.00 (3H, s), 6.94 (1H, s), 7.11 (1H, d), 7.40 (1H, m), 7.50 (1H, m), 7.61 (1H, d), 8.19 (1H, s). | 202–204° C. |
| 125 |  | 2.21 (3H, s), 2.44 (3H, s), 3.04 (4H, t), 3.77 (4H, t), 4.05 (3H, s), 6.97 (1H, m), 7.49 (4H, m), 8.01 (2H, m), 8.27 (1H, m), 8.43 (1H, s). | 103–104° C. |
| 126 |  | 2.22 (3H, s), 2.43 (3H, s), 3.39 (4H, t, J = 5.0 Hz), 4.02 (3H, s), 4.17 (4H, t), 6.87 (1H,d), 6.91(1H,d), 6.96(1H,s), 7.24 (2H, m), 8.12 (1H, s). | 168–169° C. |
| 127 |  | 2.21 (3H, s), 2.42 (3H, s), 3.38 (4H, t, J = 5.0 Hz), 4.02 (3H, s), 4.17 (4H, t), 6.87 (1H, s), 6.91 (2H, d), 6.96 (1H, s), 8.12 (1H, s). | oil phase |
| 128 | C$_{20}$H$_{26}$N$_4$O$_2$S$_1$: theoretical, C, 62.15, H, 6.78, N, 14.50, S, 8.49, experimental, | 2.17 (3H, s), 2.36 (3H, s), 3.30 (4H, t), 3.19 (3H, s), 3.96 (3H, s), 4.21 (4H, t), 6.05 (4H, m), 8.03 (1H, s). | 160–161° C. |

-continued

| example number | elementary analysis | $^1$H NMR (500 MHz, CDCl$_3$) δ | melting point |
|---|---|---|---|
| | N, 14.70, S, 8.48 | | |
| 129 | | 2.21 (3H, s), 2.36 (3H, s), 3.37 (4H, t), 3.79 (6H, s), 3.96 (3H, s), 4.10 (4H, t), 6.10 (2H, m), 7.46 (1H, s), 8.10 (1H, s). | 166–167° C. |
| 130 | | 2.11 (2H, m), 2.87 (4H, m), 3.12 (4H, t, J = 4.95 Hz), 3.70 (4H, t, J = 4.8 Hz), 3.89 (3H, s), 4.00 (3H, s), 6.89 (2H, m), 7.05 (2H, m), 8.26 (1H, s). | 130–131° C. |
| 131 | | 2.12 (2H, m), 2.87 (4H, m), 3.27 (4H, t, J = 5.0 Hz), 3.67 (4H, t, J = 5.0 Hz), 4.00 (3H, s), 6.80 (1H, m), 6.90 (2H, m), 7.21 (1H, m), 8.23 (1H, s). | 142–146° C. |
| 132 | | 2.12 (2H, m), 2.87 (4H, m), 3.27 (4H, t, J = 5.0 Hz), 3.68 (4H, t, J = 5.0 Hz), 4.00 (3H, s), 6.97 (3H, m), 7.07 (1H, m), 8.24 (1H, s). | 152–153° C. |
| 133 | | 1.76 (2H, m), 1.83 (2H, m), 2.68 (2H, t, J = 5.7 Hz), 2.72 (2H, t, J = 5.9 Hz), 3.13 (4H, t), 3.71 (4H, t), 3.89 (3H, s), 3.97 (3H, s), 6.95 (4H, m), 8.09 (1H, s). | oil phase |
| 134 | | 1.75 (2H, m), 1.83 (2H, m), 2.68 (2H, t, J = 6.1 Hz), 2.75 (2H, t, J = 6.0 Hz), 3.27 (4H, t, J = 5.15 Hz), 3.67 (4H, t, J = 4.9 Hz), 4.00 (3H, s), 6.81 (1H, d), 6.90 (2H, m), 7.20 (1H, m), 8.08 (1H, s). | oil phase |
| 135 | | 1.76 (2H, m), 1.84 (2H, m), 2.68 (2H, t), 2.72 (2H, t), 3.14 (4H, t, J = 5.0 Hz), 3.68 (4H, t, J = 5.0 Hz), 3.97 (1H, s), 6.99 (1H, s), 7.00 (2H, m), 7.09 (2H, m), 8.08 (1H, s). | 134–135° C. |
| 136 | | 0.90 (3H, s), 0.91 (3H, s), 2.07 (2H, m), 2.48 (3H, d), 3.22 (4H, t), 3.80 (4H, t), 3.88 (3H, s), 3.99 (3H, s), 6.67 (1H, s), 6.94 (1H, s), 6.98 (3H, m), 8.24 (1H, s). | oil phase |
| 137 | | 0.90 (3H, s), 0.91 (3H, s), 2.07 (1H, m), 2.49 (3H, d), 3.29 (3H, t, J = 5.0 Hz), 3.74 (4H, t, J = 4.8 Hz), 4.00 (3H, s), 6.69 (1H, m), 6.89 (2H, m), 7.21 (1H, m), 8.24 (1H, m). | oil phase |
| 138 | | 0.91 (3H, s), 0.92 (3H, s), 2.08 (1H, m), 2.54 (3H, d), 3.32 (4H, t), 3.95 (4H, t), 4.20 (3H, s), 6.70 (1H, d), 6.93 (1H, s), 7.14 (3H, m), 8.26 (1H, s). | oil phase |
| 139 | | 3.03 (4H, t), 3.69 (4H, t), 3.78 (3H, s), 4.02 (3H, s), 6.89 (4H, m), 7.04 (1H, s), 7.77 (1H, dd), 8.40 (1H, dd). | 168–169° C. |
| 140 | | 3.13 (4H, t), 3.71 (4H, t), 3.89 (3H, s), 4.02 (3H, s), 6.84 (4H, m), 6.91 (1H, m), 7.05 (1H, m), 7.78 (1H, m), 8.42 (1H, m), | 173–174° C. |
| 141 | | 3.27 (3H, t, J = 5.0 Hz), 3.69 (4H, t), 4.03 (3H, s), 6.89 (1H, m), 7.04 (1H, s), 7.32 (2H, m), 7.78 (1H, dd), 8.40 (1H, dd). | 133–135° C. |
| 142 | | 3.28 (4H, t, J = 5.2 Hz), 3.69 (4H, t, J = 5.0 Hz), 4.03 (3H, s), 6.83 (1H, m), 6.90 (3H, m), 7.20 (1H, m), 7.79 (1H, m), 8.40 (1H, m). | 95–96° C. |
| 143 | | 1.17 (3H, t, J = 7.5 Hz), 2.37 (3H, s), 2.54 (2H, q), 3.17 (4H, t, J = 3.2 Hz), 3.66 (4H, t), 3.98 (3H, s), 4.56 (1H, s), 6.93 (1H, s), 7.00 (2H, m), 8.19 (1H, s). | 225–227° C. |
| 144 | | 1.16 (3H, t, J = 7.5 Hz), 2.40 (3H, s), 2.54 (2H, q, J = 7.5 Hz), 3.07 (4H, t), 3.49 (4H, t), 3.95 (3H, s), 4.34 (2H, d), 4.53 (1H, s), 6.97 (2H, m), 7.32 (1H, s), 7.79 (1H, s). | 143–145° C. |
| 145 | | 1.11 (3H, t, J = 7.5 Hz), 2.30 (3H, s), 2.42 (2H, q), 3.04 (4H, t), 3.48 (4H, t), 4.06 (2H, d), 4.28 (2H, d), 4.36 (1H, s), 6.97 (2H, m), 7.34 (1H, s), 7.84 (1H, s). | oil phase |
| 146 | | 1.22 (3H, t), 2.29 (3H, s), 2.37 (2H, q), 3.13 (4H, t), 3.41 (4H, t), 3.56 (2H, d), 4.27 (4H, s), 6.90 (3H, m), 7.04 (5H, s), 7.25 (5H, s). | |
| 147 | | 0.91 (3H, s), 1.02 (3H, s), 1.28 (3H, t), 2.48 (3H, s), 3.04 (4H, t), 3.54 (4H, t), 4.36 (2H, q), 5.98 (2H, d), 6.90 (3H, m), 7.68 (1H, s). | oil phase |

-continued

| example number elementary analysis | $^1$H NMR (500 MHz, CDCl$_3$) δ | melting point |
|---|---|---|
| 148 | 1.14 (3H, t, J = 7.5 Hz), 2.35 (3H, s), 2.43 (2H, q, J = 7.5 Hz), 3.51 (4H, t, J = 4.6 Hz), 3.90 (4H, t, J = 4.6 Hz), 3.92 (3H, s), 6.19 (1H, d), 7.21 (2H, dd), 7.65 (1H, m), 7.78 (1H, s). | 158–159° C. |
| 149 | 1.09 (3H, t, J = 7.5 Hz), 2.38 (3H, s), 2.54 (2H, q, J = 7.5 Hz), 3.31 (4H, t, J = 5.0 Hz), 3.63 (4H, t, J = 5.0 Hz), 3.92 (3H, s), 6.84 (1H, d), 6.96 (2H, dd), 7.21 (1H, d), 7.69 (1H, s). | 198–199° C. |

Antitumor activities of the compounds of present invention were tested. Antitumor activities of compounds of the present invention were tested in vitro against 5 kinds of human tumor cell lines and 2 kinds of leukemia tumor cell lines. The method of in vitro test is as follows.

Example 1)

In Vitro Antitumor Effect Against Human Tumor Cell Lines

A. Tumor cell line:
A549 (human non-small lung cell)
SKOV-3 (human ovarian)
HCT-15 (human colon)
XT 498 (human CNS)
SKMEL 2 (human melanoma)

B. Method of test(SRB Assay Method)

a. Human solid tumor cell lines, A594(non-small lung cell), SKMEL-2(melanoma), HCT-15(colon), SKOV-3 (ovarian), XF-498(CNS) were cultured at 37° C., in 5% $CO_2$ incubater using the RPMI 1640 media containing 10% FBS, while they were transfer-cultured successively once or twice per week. Cell cultures were dissolved into the solution of 0.25% trypsin and 3 mM CDTA PBS(−) and then cells were separated from media which the cells were sticked on.

b. 5×10$^3$–2×10$^4$ cells were added into each well of 96-well plate and cultured in 5% $CO_2$ incubater, at 37° C., for 24 hours.

c. Each sample drugs was dissolved in a small quantity of DMSO, and diluted to concentrations prescribed in experiment with media, and then the final concentration of DMSO was controlled below 0.5%.

d. A medium of each well cultured for 24 hours as above b., was removed by aspiration. 200 μl of drug samples prepared in c. was added into each well and the wells were cultured for 48 hours. Tz(time zero) plates were collected at the point of time drugs were added.

e. After Tz plates and plates were treated with cell fixing by TCA of SRB assay method, staining of 0.4% SRB solution, washing with 1% acetic acid, OD values were measured at 520 nm, following elution of dye with 10 mM Tris solution.

C. Calculation of Result a. Time zero(Tz) value was determined by obtainment of SRB protein value at the point of time drugs were added.

b. Control value(C) was determined with OD value of well that was not added with drug.

c. Drug-treated test value(T) was determined with OD value of well treated with dug.

d. Drug effects of growth stimulation, net growth inhibition, net killing etc. were determined with Tz, C and T.

e. If T≧Tz, cellular response function was calculated with 100×(T−Tz)/(C−Tz), and if T<Tz, with 100×(T−Tz)/Tz. The results are shown in the next table.

Reference

1) P. Skehan, R. Strong, D Scudiero, A. Monks, J. B. Mcmahan, D. T. Vistica, J. Warren, H. Bokesh, S. Kenny and M. R. Boyd : Proc. Am. Assoc. Cancer Res., 30, 612(1989)

2) L. V. Rubinstein, R. H. Shoemarker, K. D. Paull, R. M. simon, S. Tosini, P. Skehan, D. Scudiero, A. Monks and M. R. boyd.; J. Natl. Cancer Inst., 82, 1113(1990)

3) P. Skehan, R. Strong, D. Scudiero, A. Monks, J. B. Memahan, D. t. Vistica, J. Warren, H. Bokesh, S. Kenny and M. R. Boyd.; J. Natl. Cancer ins., 82, 1107(1990)

D. Results.

It was found that the compounds of present invention have the superior antitumor activities to those of the control, cisplatin against 5 kinds of human solid cancer cell lines. Especially, compounds of example 1), 6), 13), 16), 28), 29), 38), 41), 47), 48), 49), 50), 55), 61), 91), 97), 98), 100), 108), 109), 111), 113), 115), 118), 119), 120), 121), 126), 128), 129), 144), 148), 149) have superior antitumor activities to those of cisplatin.

| EXAMPLE NUMBER | NET GROWTH AS % OF CONTROL (Conc. μg/mL) | | | | |
|---|---|---|---|---|---|
| | A594 | SK-OV-3 | SK-MEL-2 | XF-498 | HCT-15 |
| 1 | 0.1372 | 0.0269 | 0.0172 | 0.1149 | 0.0479 |
| 6 | 0.0091 | 0.0072 | 0.0092 | 0.0156 | 0.0108 |
| 8 | 1.1428 | 0.3930 | 0.8302 | 1.2938 | 1.0499 |
| 13 | 0.2483 | 0.0697 | 0.1771 | 0.2769 | 0.0829 |
| 16 | 0.4491 | 0.0263 | 0.0182 | 0.1662 | 0.1160 |
| 18 | 1.0813 | 0.7207 | 0.8138 | 0.8275 | 0.6850 |
| 21 | 1.9952 | 1.0423 | 1.7609 | 2.8475 | 0.6684 |
| 22 | 2.2086 | 1.2588 | 1.8210 | 2.3352 | 0.6764 |
| 23 | 1.9836 | 0.5929 | 0.8665 | 2.2896 | 1.0053 |
| 28 | 0.5958 | 0.3192 | 0.6495 | 0.7663 | 0.3756 |
| 29 | 0.0002453 | 0.0001310 | 0.0007708 | 0.0001901 | 0.0007707 |
| 38 | 0.4266 | 0.0709 | 0.0833 | 0.2836 | 0.0652 |
| 41 | 0.4464 | 0.0836 | 0.0981 | 0.3818 | 0.0878 |
| 47 | 0.3693 | 0.2094 | 0.4384 | 0.4998 | 0.2975 |
| 48 | 0.0913 | 0.0583 | 0.0954 | 0.1430 | 0.0498 |
| 49 | 0.0917 | 0.0223 | 0.0723 | 0.0955 | 0.0946 |
| 50 | 0.0984 | 0.0732 | 0.0954 | 0.0736 | 0.0828 |
| 55 | 0.5074 | 0.1088 | 0.2812 | 0.4094 | 0.1577 |
| 60 | 2.8176 | 1.7486 | 0.6468 | 2.1795 | 0.3410 |
| 61 | 0.8539 | 0.1710 | 0.1594 | 0.4343 | 0.0910 |
| 62 | 3.5875 | 0.2431 | 0.2894 | 1.1457 | 0.2950 |
| 91 | 0.5284 | 0.3156 | 0.5562 | 0.9176 | 0.5979 |
| 97 | 0.3518 | 0.0536 | 0.01778 | 0.2965 | 0.1489 |
| 98 | 0.3489 | 0.0645 | 0.1822 | 0.2229 | 0.1801 |
| 100 | 0.0016111 | 0.0015197 | 0.0032233 | 0.0020713 | 0.0065666 |
| 108 | 0.1158 | 0.0797 | 0.1277 | 0.1352 | 0.0741 |
| 109 | 0.1088 | 0.0832 | 0.1079 | 0.1494 | 0.0581 |
| 111 | 0.1611 | 0.0661 | 0.1258 | 0.0949 | 0.0749 |
| 113 | 0.4371 | 0.1680 | 0.3368 | 0.5967 | 0.0973 |
| 115 | 0.6168 | 0.2201 | 0.3672 | 1.4025 | 0.2081 |
| 118 | 0.0038 | 0.0011 | 0.0046 | 0.0042 | 0.0024 |
| 119 | 0.3824 | 0.1129 | 0.2414 | 0.5133 | 0.2026 |
| 120 | 0.0001299 | 0.0000226 | 0.0002677 | 0.0001193 | 0.0001265 |

-continued

| EXAMPLE NUMBER | NET GROWTH AS % OF CONTROL (Conc. μg/mL) | | | | |
|---|---|---|---|---|---|
| | A594 | SK-OV-3 | SK-MEL-2 | XF-498 | HCT-15 |
| 121 | 0.0116039 | 0.0020599 | 0.0177227 | 0.0087927 | 0.0070088 |
| 126 | 0.006171 | 0.0005225 | 0.0110493 | 0.0048476 | 0.0058752 |
| 127 | 1.5462 | 0.4162 | 0.4776 | 1.3486 | 0.5366 |
| 128 | 0.0059411 | 0.0013953 | 0.0127665 | 0.0039702 | 0.0065951 |
| 129 | 0.0000119 | 0.0000033 | 0.0000389 | 0.0000117 | 0.0000384 |
| 144 | 1.0350 | 0.6289 | 0.6060 | 4.4550 | 0.4738 |
| 148 | 0.6767 | 0.3129 | 0.1582 | 0.7615 | 0.3203 |
| 149 | 0.3883 | 0.1819 | 0.1731 | 0.4255 | 0.0471 |
| Cisplatin | 0.8184 | 0.7134 | 0.7147 | 0.7771 | 3.0381 |

Example 2)

* In Vitro Antituimor Effects Against Animal Leukemia Cells.

A. Material of Experiment

Tumor cell lines:

L1210(mouse leukemia cell)

P388 (mouse lymphoid neoplasma cell)

B. Method of Experiment(Dye Exclusion Assay)

1) L-1210 and P388 cells that were cultured in RPMI 1640 media containing 10% FBS were regulated as the cell concentration of $1 \times 10^6$ cells/ml.

2) Sample drugs diluted with log dose were added into the cells, and it were cultured at 37° C., for 48 hours, in 50% $CO_2$ incubater, and then viable cell number was measured. Viable cell number was measured with dye exclusion test using trypan blue.

3) The concentration of sample compounds of 50% cell growth inhibition compared with standard group was determined as $IC_{50}$. The results are shown at the next table.

* Reference

1) P. Skehan, R. Strong, D. Scudiero, A. Monks, J. B. Mcmahan, D. T. Vistica, J. Warren, H. Bokesh, s. Kenney and M. R. Boyd.: Proc. Am. Assoc. Cancer Res., 30, 612(198).

2) I. V. Rubinstein, R. H. Shoemaker, K. D. Paull, R. M. Simon, s. Tosini, P. Skehan, D. Scudiero, A. Monks, J. Natl. Cancer Inst., 82, 1113(1990)

3) P. Skellan, R. Strong, D. Scudiero, J. B. Mcmanhan, D. T. Vistica, J. Warren, H. Bokesch, S. Kenney and M. R. Boyd.: J. Natl. Cancer Inst., 82, 1107(1990)

C. Result

As the results of measurement of antitumor activities of compounds of the present invention against L1210 and P388 mouse cancer cells, it was found that compounds of example 1), 6), 13), 16), 29), 38), 41), 47), 48), 49), 108), 118), 120), 128), 148), 149) had same or more excellent antitumor activities than those of the control drug, mytomicin C.

| EXAMPLE NUMBER | ED$_{50}$ (μg/mL) | |
|---|---|---|
| | L1210 | P388 |
| 1 | 1.6 | 0.6 |
| 6 | 0.6 | 0.3 |
| 13 | 1.7 | 1.6 |
| 16 | 1.8 | 1.6 |
| 29 | 0.4 | 0.5 |
| 38 | 1.4 | 1.0 |
| 41 | 1.4 | 2.0 |
| 47 | 0.3 | 0.3 |
| 48 | 1.9 | 1.8 |
| 49 | 1.3 | 0.6 |
| 50 | 2.0 | 1.5 |
| 97 | 2.0 | 1.6 |
| 98 | 2.0 | 2.1 |
| 108 | 0.8 | 0.9 |
| 118 | 0.06 | 0.06 |
| 119 | 2.2 | 2.0 |
| 120 | 0.3 | 0.1 |
| 128 | 0.5 | 0.2 |
| 148 | 1.5 | 1.3 |
| 149 | 0.9 | 1.6 |
| mitomycin C | 1.6 | 1.1 |

In vivo antitumor activity test was carried out in mice with samples having significance in in vitro test.

Example 3)

* In Vivo Antitumor Effects Against Mouse Leukemia P388 Cells.

A. Material of Experiment

BDFI mice were used.

B. Method of Experiment

1) Leukemia P388 cells being transfer-cultured succesively in DBA/2 mouse, were grafted i.p. into each mouse of a group comprising 8 mice of 6 week old BDFI mouse as the dose of $1 \times 10^6$ cells/0.1 ml.

2) Sample drugs were dissolved in PBS or suspended in 0.5% Tween 80, and then injected into abdominal cavity of mouse at each prescribed concentration on days 1, 5, 9, respectively.

3) With observation every day, survival times of tested mice were measured. Antitumor activities was determined in such a manner that the increasing ratio(T/C %) of average survival days of drug-treated groups compared with the control group was calculated using the mean survival times of each tested groups.

The results are shown at the next table.

* Reference

A. Goldin, J. M. Venditti, J. S. Macdonald, F. M. Muggia, J. E. Henney and V. T. DeVita.: Euro. J. S. Macdonald, F. M. Muggia, J. E. Henney and V. T. DeVita: Euro. J. Cancer, 17, 129 (1981).

* Experimental Conditions for Mouse P388

Animal: BDFI mouse (8 mice/group)

Tumor: mouse P388

Inoculum size: $10^6$ cells/mouse

Inoculum site: i. p.

Treatment site: i. p.

Treatment time: days 1, 5, 9

Parameter: median survival time

Criteria: T/C %

C. Result

Through in vivo experiment using P388 mouse cancer cells, significant antitumor effect of the compounds of example 1), 6), 16), 29) were observed.

| Example No. | Dose (mg/kg) | T/C (%) | etc. |
|---|---|---|---|
| 1 | 100 | 134.6 | |
| | 50 | 109.1 | |
| 6 | 100 | 183.3 | |
| | 50 | 133.3 | |

-continued

| Example No. | Dose (mg/kg) | T/C (%) | etc. |
|---|---|---|---|
| 16 | 100 | 131.8 | |
| | 50 | 113.6 | |
| 29 | 100 | 190.9 | |
| | 50 | 136.4 | |

Example 4)

\* In Vivo Antitumor Activities Against Mouse Solid Tumor, 1316 Melanoma.

A. Material of Experiment.

BDF1 mouse was used in experiment while being successively transfer cultured in C57BL/6 mice by s.c.

B. Methods

1) After 1 g of tumor was added into cold balanced salt solution up to be 10 ml, it was homogenized (10:1.brei).

2) 0.5 ml Brei of the above 1) were grafted into each BDFI mouse by i.p.

3) Median survival time was measured, and the activity was determined in such a manner that if T/C was over 125%, it presented moderate activity, while if it is over 150%, it had significant activity.

The results are shown at the next table.

\*Reference

A. Goldin, J. M. Venditti, J. S. Macdonald, F. M. Muggia, J. E. Henney and V. T. DeVita, Euro. J. Cancer, 17, 129 (1981).

\* Experimental Conditions for Mouse B16 Melanoma.
Animal: BDFI mouse (8 mice/group)
Inoculum size: $10^5$ cells/mouse
Inoculum site: i. p.
Treatment site: i. p.
Treatment time: days 1, 5, 9
Parameter: median survival time
Criteria: T/C %

C. Results

With in vivo experiment using B16 mouse melanoma solid tumor, it was observed that the compounds of examples 6), 16) etc. have the significant antitumor activities.

| Example No. | Dose | T/C (%) | Etc. |
|---|---|---|---|
| 6 | 200 | 139.4 | |
| | 100 | 124.2 | |
| | 50 | 127.3 | |
| 16 | 200 | 118.2 | |
| | 100 | 127.3 | |
| | 50 | 115.2 | |

Example 5)

\* Acute Toxicity Test ($LD_{50}$)

Litchfield-Wilcoxon Method.

6 week old ICR mice(male 30±2.0 g) was fed freely with solid feed and water at room temperature, 23±1° C. and at humidity 60±5%. Sample drugs were injected into the abdominal cavities of mice, while each goup comprises 6 mice.

Observed during 14 days, external appearances and life or dead were recorded, and then, visible pathogenies were observed from dead animals by dissection. $LD_{50}$ value was calculated by Litchfiled-wilcoxon method.

The results are shown at the next table.

| | $LD_{50}$ (mg/ml) | |
|---|---|---|
| Example No. | i.p. | p.o. |
| 6 | 248.5 | >622 |
| 28 | >1,800 | >2,000 |
| 61 | >1,687 | |
| 97 | 1,100 | |
| 98 | >1,800 | >2,000 |
| 108 | >2,000 | >3,110 |
| 109 | 2,000 | >2,073 |
| 118 | 182.8 | 571.8 |
| 148 | 425.3 | |
| 149 | 410.5 | |
| cisplatin | 21.4 | |

As described above, it was found that the compouds of the present invention are more safer and have superior antitumor activities to cisplatin, and accordingly have solved the problems of drugs by the prior art such as restriction of dosage, toxicity, etc.

Examples of Pharmaceutical Preparations

Tablets: (Examples 1–4)

Tablet(250 mg) was prepared with the ingredients of the following table by conventional tablet manufacturing method.

| Examples | ingredients (mg) | |
|---|---|---|
| 1 | compound of example 1 | 20 |
| | lactose | 120 |
| | microcrystalline cellulose | 30 |
| | corn starch | 40 |
| | povidone | 30 |
| | sodium starch glycolate | 8 |
| | magnesium stereate | 2 |
| 2 | compound of example 148 | 20 |
| | lactose | 110 |
| | microcrystalline cellulose | 40 |
| | corn starch | 45 |
| | povidone | 25 |
| | sodium starch glycolate | 8 |
| | magnesium stearate | 2 |
| 3 | compound of example 16 | 20 |
| | lactose | 120 |
| | microcrystalline cellulose | 35 |
| | corn starch | 35 |
| | povidone | 30 |
| | sodium starch glycolate | 8 |
| | magnesium stearate | 2 |
| 4 | compound of example 149 | 20 |
| | lactose | 100 |
| | microcrystalline cellulose | 45 |
| | corn starch | 50 |
| | povidone | 25 |
| | sodium starch glycolate | 8 |
| | magnesium stearate | 2 |

Capsules(Example 5–8)

Capsule(250 mg) was prepared with the ingredients of the following table by conventional capsule manufacturing method.

| Examples | ingredients (mg) | |
|---|---|---|
| 5 | compound of example 1 | 10 |
| | lactose | 100 |
| | corn starch | 100 |
| | povidone | 30 |

| Examples | ingredients (mg) | |
|---|---|---|
|  | sodium starch glycolate | 7 |
|  | magnesium stearate | 3 |
| 6 | compound of example 148 | 10 |
|  | lactose | 105 |
|  | corn starch | 100 |
|  | povidone | 25 |
|  | sodium starch glycolate | 7 |
|  | magnesium stearate | 3 |
| 7 | compound of example 16 | 10 |
|  | lactose | 90 |
|  | corn starch | 110 |
|  | povidone | 30 |
|  | sodium starch glycolate | 7 |
|  | magnesium stearate | 3 |
| 8 | compound of example 149 | 10 |
|  | lactose | 95 |
|  | corn starch | 110 |
|  | povidone | 25 |
|  | sodium starch glycolate | 7 |
|  | magnesium stearate | 3 |

Injectable Preparations (Examples 9–16)

Injectable preparations(5 ml of ampoule and vial) were prepared with the ingredients of the following tables by the conventional injection manufacturing method.

| Examples (ampoule) | ingredients | |
|---|---|---|
| 9 | compound of example 1 | 30 mg |
|  | polyoxy 35 castor oil | 4000 mg |
|  | absolute ethanol | 1.17 ml |
|  | distilled water for inj. | q.s. |
| 10 | compound of example 148 | 30 mg |
|  | polyoxy 35 castor oil | 3200 mg |
|  | absolute ethanol | 1.97 ml |
|  | distilled water for inj. | q.s. |
| 11 | compound of example 16 | 30 mg |
|  | polyoxy 35 castor oil | 3500 mg |
|  | absolute ethanol | 1.68 ml |
|  | distilled water for inj. | q.s. |
| 12 | compound of example 149 | 30 mg |
|  | polyoxy 35 castor oil | 3000 mg |
|  | absolute ethanol | 2.16 ml |
|  | distilled water for inj. | q.s. |
| Example 13 (vial) | compound of example 1 | 30 mg |
|  | polyoxy 35 castor oil | 4000 mg |
|  | absolute ethanol | 1.17 ml |
|  | distilled water for inj. | q.s. |
| 14 | compound of example 148 | 30 mg |
|  | polyoxy 35 castor oil | 3200 mg |
|  | absolute ethanol | 1.97 ml |
|  | distilled water for inj. | q.s. |
| 15 | compound of example 16 | 30 mg |
|  | polyoxy 35 castor oil | 3500 mg |
|  | absolute ethanol | 168 ml |
|  | distilled water for inj. | q.s. |
| 16 | compound of example 149 | 30 mg |
|  | polyoxy 35 castor oil | 3000 mg |
|  | absolute ethanol | 2.16 ml |
|  | distilled water for inj. | q.s. |

Ointment(Examples 17–20)

Ointment(1 g) was prepared with the ingredients of the following table by the conventional ointment manufacturing method.

| Examples | ingredients (mg) | |
|---|---|---|
| 17 | compound of example 1 | 6 |
|  | polyoxy 40 hydrogenated castor oil | 350 |
|  | absolute ethanol | 100 |
|  | sodium p-oxybenzoate | 1.5 |
|  | $NaH_2PO_4$ | 1.06 |
|  | citric acid | 1.48 |
|  | propyleneglycol | 200 |
|  | glycerine | 150 |
|  | cetostearyl alcohol | 50 |
|  | cetiol H. E. | 130 |
|  | purified water | q.s. |
| 18 | compound of example 148 | 6 |
|  | polyoxy 40 hydrogenated castor oil | 300 |
|  | absolute ethanol | 100 |
|  | sodium p-oxybenzoate | 1.5 |
|  | $NaH_2PO_4$ | 1.06 |
|  | citric acid | 1.48 |
|  | propyleneglycol | 200 |
|  | glycerine | 150 |
|  | cetostearyl alcohol | 50 |
|  | cetiol H. E. | 145 |
|  | purified water | q.s. |
| 19 | compound of example 16 | 6 |
|  | polyoxy 40 hydrogenated castor oil | 350 |
|  | absolute ethanol | 150 |
|  | sodium p-oxybenzoate | 1.5 |
|  | $NaH_2PO_4$ | 1.06 |
|  | citric acid | 1.48 |
|  | propyleneglycol | 150 |
|  | glycerine | 150 |
|  | cetostearyl alcohol | 100 |
|  | cetiol H. E. | 135 |
|  | purified water | q.s. |
| 20 | compound of example 149 | 6 |
|  | polyoxy 40 hydrogenated castor oil | 300 |
|  | absolute ethanol | 100 |
|  | sodium p-oxybenzoate | 1.5 |
|  | $NaH_2PO_4$ | 1.06 |
|  | citric acid | 1.48 |
|  | propyleneglycol | 200 |
|  | glycerine | 100 |
|  | cetostearyl alcohol | 100 |
|  | cetiol H. E. | 147 |
|  | purified water | q.s. |

Suppository(Examples 21–24)

Suppository(1 g) was prepared with the ingredients of the following table by conventional suppository manufacturing method.

| Example | ingredients (mg) | |
|---|---|---|
| 21 | compound of example 1 | 6 |
|  | polyoxy 35 castor oil | 250 |
|  | glycerine | 80 |
|  | propyleneglycol | 50 |
|  | stearyl alcohol | 50 |
|  | stearic acid | 50 |
|  | Witepsol ® | 364 |
|  | glycerylmonostearate | 150 |
| 22 | compound of example 148 | 6 |
|  | polyoxy 35 castor oil | 230 |
|  | glycerine | 80 |
|  | propyleneglycol | 70 |
|  | stearyl alcohol | 50 |
|  | stearic acid | 50 |
|  | Witepsol ® | 414 |
|  | glycerylmonostearate | 100 |
| 23 | compound of example 16 | 6 |
|  | polyoxy 35 castor oil | 245 |
|  | glycerine | 80 |
|  | propyleneglycol | 65 |
|  | stearyl alcohol | 70 |
|  | stearic acid | 60 |
|  | Witepsol ® | 394 |
|  | glycerylmonostearate | 80 |
| 24 | compound of example 149 | 6 |
|  | polyoxy 35 castor oil | 225 |

| Example | ingredients (mg) | |
|---|---|---|
| | glycerine | 70 |
| | propyleneglycol | 60 |
| | stearyl alcohol | 55 |
| | stearic acid | 50 |
| | Witepsol® | 459 |
| | glycerylmonostearate | 75 |

Oral solution(example 25o28)

Oral solution(100 ml) was prepared with the ingredients of the following tables by the conventional oral solution manufacturing method.

| Example | ingredients | |
|---|---|---|
| 25 | compound of example 1 | 30 mg |
| | polyoxy 40 hydrogenated castor oil | 30 g |
| | absolute ethanol | 2 ml |
| | propyleneglycol | 15 g |
| | polyethyleneglycol 400 | 10 g |
| | Tween 80 | 5 g |
| | methy p-oxybenzoate | 0.1 g |
| | purified sugar | 12 g |
| | herb perfume | 0.1 ml |
| | purified water | q.s. |
| 26 | compound of example 148 | 30 mg |
| | polyoxy 35 castor oil | 30 g |
| | absolute ethanol | 2 ml |
| | propyleneglycol | 12 g |
| | polyethyleneglycol | 15 g |
| | Tween 80 | 10 g |
| | methyl p-oxybenzoate | 0.1 g |
| | purified sugar | 12 g |
| | herb perfume | 0.1 ml |
| | purified water | q.s. |
| 27 | compound of example 16 | 30 mg |
| | polyoxy 35 castor oil | 25 g |
| | absolute ethanol | 2 ml |
| | propyleneglycol | 20 g |
| | polyethyleneglycol 400 | 15 g |
| | Tween 80 | 7 g |
| | methyl p-oxybenzoate | 0.1 g |
| | purified sugar | 15 g |
| | herb perfume | 0.15 ml |
| | purified water | q.s. |
| 28 | compound of example 149 | 30 mg |
| | polyoxy 35 castor oil | 30 g |
| | absolute ethanol | 2 ml |
| | propyleneglycol | 17 g |
| | polyethyleneglycol 400 | 12 g |
| | Tween 80 | 10 g |
| | methyl p-oxybenzoate | 0.1 g |
| | purified sugar | 13 g |
| | herb perfume | 0.15 ml |
| | purified water | q.s. |

Troche(Examples 29–32)

Troche(500 mg) was prepared with the ingredients of the following table by conventional troche manufacturing method.

| Example | ingredients (mg) | |
|---|---|---|
| 29 | compound of example 1 | 20 |
| | mannitol | 300 |
| | sugar | 100 |
| | corn starch | 40 |
| | povidone | 30 |
| | sodium starch glycoate | 8 |
| | magnesium stearate | 2 |
| 30 | compound of example 148 | 20 |
| | mannitol | 280 |

| Example | ingredients (mg) | |
|---|---|---|
| | sugar | 120 |
| | corn starch | 45 |
| | povidone | 25 |
| | sodium starch glycolate | 8 |
| | magnesium stearate | 2 |
| 31 | compound of example 16 | 20 |
| | mannitol | 320 |
| | sugar | 100 |
| | corn starch | 20 |
| | povidone | 30 |
| | sodium starch glycolate | 8 |
| | magnesium stearate | 2 |
| 32 | compound of example 149 | 20 |
| | mannitol | 300 |
| | sugar | 110 |
| | corn starch | 50 |
| | povidone | 10 |
| | sodium starch glycolate | 8 |
| | magnesium stearate | 2 |

What is claimed is:

1. A compound of the general formula (I)

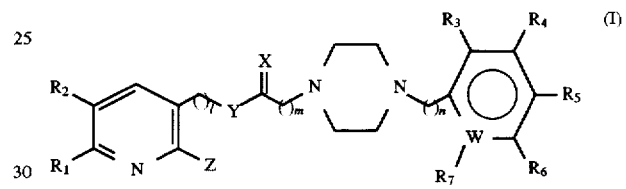

wherein $R_1$ and $R_2$ are independently selected from the group consisting of hydrogen, and $C_1$–$C_8$ alkyl;

$R_3$, $R_4$, $R_5$, $R_6$ and $R_7$ are independently selected from the group consisting of hydrogen, halogen, hydroxy, nitro, —$OCOC_1$–$C_4$ lower alkyl, $C_1$–$C_4$ lower alkyl, $C_1$–$C_4$ lower alkoxy, phenyl, and —$NR^xR^y$, wherein $R^x$ and $R^y$ are independently selected from the group consisting of hydrogen, $C_1$–$C_4$ lower alkyl, $C_2$–$C_4$ unsaturated lower alkyl, phenyl and benzyl;

l is an integer of 0, 1, 2, 3, 4, 5, 6 or 7;

m and n are independently an integer of 0 or 1;

W is carbon or nitrogen;

X is selected from the group consisting of oxygen and sulfur;

Y is NH or oxygen; and

Z is selected from the group consisting of $C_1$–$C_8$ alkoxy, phenoxy, $C_1$–$C_4$ alkylamine and oxo group, provided that when Z is an oxo group the compound is of the general formula (I')

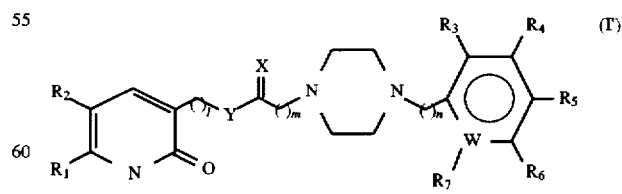

wherein $R_1$, $R_2$, $R_3$, $R_4$, $R_5$, $R_6$, $R_7$, l, m, n, W, X and Y are as defined above; or a pharmaceutically acceptable acid addition salt thereof.

2. The compound according to claim 1, which is a compound of the formula (I'):

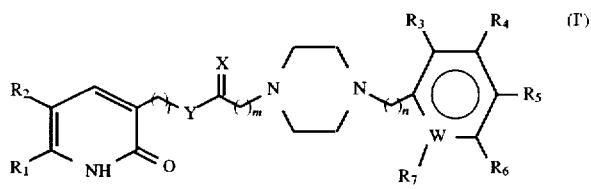

wherein $R_1$, $R_2$, $R_3$, $R_4$, $R_5$, $R_6$, $R_7$, l, m, n, W, X and Y are as defined above.

3. The compound according to claim 1, wherein W is carbon.

4. The compound according to claim 1, wherein W is nitrogen.

5. A pharmaceutical composition, comprising:

an pharmaceutically effective amount of the compound as set forth in claims 1 or 2; and one or more conventional adjuvents.

6. The pharmaceutical composition according to claim 5, wherein said conventional adjuvent is selected from the group consisting of conventional vehicles, binding agent, degrading agent, lubricating agent, dissolving agent, aids for dissolution, stabilizing agent, base of ointment, pH-adjusting agent and perfume.

* * * * *